(12) United States Patent
Van Pel et al.

(10) Patent No.: US 7,785,881 B2
(45) Date of Patent: Aug. 31, 2010

(54) MAGE-C2 ANTIGENIC PEPTIDES AND USES THEREOF

(75) Inventors: Aline Van Pel, Brussels (BE); Daniele Godelaine, Brussels (BE); Javier Carrasco, Brussels (BE); Francis Brasseur, Brussels (BE); Thierry Boon-Falleur, Brussels (BE)

(73) Assignee: Ludwig Institute for Cancer Research, New York, NY (US)

( * ) Notice: Subject to any disclaimer, the term of this patent is extended or adjusted under 35 U.S.C. 154(b) by 127 days.

(21) Appl. No.: 12/011,726

(22) Filed: Jan. 29, 2008

(65) Prior Publication Data

US 2008/0311652 A1 Dec. 18, 2008

Related U.S. Application Data

(62) Division of application No. 11/044,051, filed on Jan. 28, 2005, now Pat. No. 7,348,007.

(60) Provisional application No. 60/542,540, filed on Feb. 9, 2004.

(51) Int. Cl.
*C12N 15/86* (2006.01)

(52) U.S. Cl. .............. 435/326; 435/252.3; 435/320.1; 536/23.1

(58) Field of Classification Search ............... 435/326, 435/252.3, 320.1; 536/23.1
See application file for complete search history.

(56) References Cited

OTHER PUBLICATIONS

Bergmann et al, 1994 (J Virol, 68(8): 5306-5310).*
Eisenlohr et al, 1992 (J Exp Med, 175: 481-487).*
Shastri et al, 1995 (J Immunol, 155: 4339-4346).*

* cited by examiner

*Primary Examiner*—Larry R. Helms
*Assistant Examiner*—Minh-Tam Davis
(74) *Attorney, Agent, or Firm*—Fulbright & Jaworski LLP

(57) ABSTRACT

This invention relates to isolated peptides derived from MAGE-C2, nucleic acid molecules that encode MAGE-C2 and the isolated peptides derived from MAGE-C2, expression vectors comprising the nucleic acid molecules, host cells transformed or transfected with the nucleic acid molecules or the expression vectors, and to tetramers comprising the peptides, HLA molecules, $\beta_2$ microglobulin and a first and second binding partner. This invention also relates to methods for using the peptides, nucleic acid molecules, expression vectors, tetramers and complexes of this invention as well as to cytolytic T cells which recognize the peptides in complex with an HLA molecule.

4 Claims, 4 Drawing Sheets

SEQUENCE LISTING

<160> NUMBER OF SEQ ID NOS: 111

<210> SEQ ID NO 1
<211> LENGTH: 9
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: Xaa at position 9 may be any amino acid

<400> SEQUENCE: 1

Ala Leu Lys Asp Val Glu Glu Arg Xaa
1               5

<210> SEQ ID NO 2
<211> LENGTH: 8
<212> TYPE: PRT
<213> ORGANISM: homo sapiens

<400> SEQUENCE: 2

Leu Lys Asp Val Glu Glu Arg Val
1               5

<210> SEQ ID NO 3
<211> LENGTH: 9
<212> TYPE: PRT
<213> ORGANISM: homo sapiens

<400> SEQUENCE: 3

Ala Leu Lys Asp Val Glu Glu Arg Val
1               5

<210> SEQ ID NO 4
<211> LENGTH: 8
<212> TYPE: PRT
<213> ORGANISM: homo sapiens

<400> SEQUENCE: 4

Ala Leu Lys Asp Val Glu Glu Arg
1               5

<210> SEQ ID NO 5
<211> LENGTH: 9
<212> TYPE: PRT
<213> ORGANISM: homo sapiens

<400> SEQUENCE: 5

Ala Leu Lys Asp Val Glu Glu Arg Ala
1               5

<210> SEQ ID NO 6
<211> LENGTH: 9
<212> TYPE: PRT
<213> ORGANISM: homo sapiens

<400> SEQUENCE: 6

Ala Leu Lys Asp Glu Glu Glu Arg Ala
1               5

<210> SEQ ID NO 7
<211> LENGTH: 9
<212> TYPE: PRT
<213> ORGANISM: homo sapiens

-continued

```
<400> SEQUENCE: 7

Ala Lys Arg Glu Glu Gly Glu Gly Val
1               5

<210> SEQ ID NO 8
<211> LENGTH: 9
<212> TYPE: PRT
<213> ORGANISM: homo sapiens

<400> SEQUENCE: 8

Ala Leu Arg Asp Glu Glu Glu Arg Ala
1               5

<210> SEQ ID NO 9
<211> LENGTH: 9
<212> TYPE: PRT
<213> ORGANISM: homo sapiens

<400> SEQUENCE: 9

Ala Leu Arg Asp Glu Glu Glu Arg Val
1               5

<210> SEQ ID NO 10
<211> LENGTH: 9
<212> TYPE: PRT
<213> ORGANISM: homo sapiens

<400> SEQUENCE: 10

Glu Ala Asp Pro Thr Gly His Ser Tyr
1               5

<210> SEQ ID NO 11
<211> LENGTH: 9
<212> TYPE: PRT
<213> ORGANISM: homo sapiens

<400> SEQUENCE: 11

Glu Val Asp Pro Ile Gly His Leu Tyr
1               5

<210> SEQ ID NO 12
<211> LENGTH: 9
<212> TYPE: PRT
<213> ORGANISM: Artificial sequence
<220> FEATURE:
<223> OTHER INFORMATION: Potential Binding Motif
<220> FEATURE:
<221> NAME/KEY: MISC_FEATURE
<222> LOCATION: (3)..(3)
<223> OTHER INFORMATION: Xaa at position 3 may be Arg or Lys
<220> FEATURE:
<221> NAME/KEY: MISC_FEATURE
<222> LOCATION: (4)..(4)
<223> OTHER INFORMATION: Xaa at position 4 may be Asp or Glu
<220> FEATURE:
<221> NAME/KEY: MISC_FEATURE
<222> LOCATION: (5)..(5)
<223> OTHER INFORMATION: Xaa at position 5 may be Val or Glu
<220> FEATURE:
<221> NAME/KEY: MISC_FEATURE
<222> LOCATION: (6)..(6)
<223> OTHER INFORMATION: Xaa at position 6 may be Glu or Gly
<220> FEATURE:
<221> NAME/KEY: MISC_FEATURE
<222> LOCATION: (8)..(8)
<223> OTHER INFORMATION: Xaa at position 8 may be Gly or Arg
<220> FEATURE:
<221> NAME/KEY: MISC_FEATURE
```

```
<222> LOCATION: (9)..(9)
<223> OTHER INFORMATION: Xaa at position 9 may be Ala or Val

<400> SEQUENCE: 12

Ala Leu Xaa Xaa Xaa Xaa Glu Xaa Xaa
1               5

<210> SEQ ID NO 13
<211> LENGTH: 9
<212> TYPE: PRT
<213> ORGANISM: Artificial sequence
<220> FEATURE:
<223> OTHER INFORMATION: Antigenic peptide

<400> SEQUENCE: 13

Ala Leu Arg Asp Val Glu Glu Arg Val
1               5

<210> SEQ ID NO 14
<211> LENGTH: 9
<212> TYPE: PRT
<213> ORGANISM: Artificial Sequence
<220> FEATURE:
<223> OTHER INFORMATION: Antigenic Peptide

<400> SEQUENCE: 14

Ala Leu Arg Asp Val Glu Glu Arg Ala
1               5

<210> SEQ ID NO 15
<211> LENGTH: 9
<212> TYPE: PRT
<213> ORGANISM: Artificial Sequence
<220> FEATURE:
<223> OTHER INFORMATION: Antigenic peptide

<400> SEQUENCE: 15

Ala Leu Arg Asp Val Glu Glu Gly Ala
1               5

<210> SEQ ID NO 16
<211> LENGTH: 9
<212> TYPE: PRT
<213> ORGANISM: Artificial Sequence
<220> FEATURE:
<223> OTHER INFORMATION: Antigenic peptide

<400> SEQUENCE: 16

Ala Leu Arg Asp Val Glu Glu Gly Val
1               5

<210> SEQ ID NO 17
<211> LENGTH: 9
<212> TYPE: PRT
<213> ORGANISM: Artificial Sequence
<220> FEATURE:
<223> OTHER INFORMATION: Antigenic peptide

<400> SEQUENCE: 17

Ala Leu Arg Asp Val Gly Glu Arg Val
1               5

<210> SEQ ID NO 18
<211> LENGTH: 9
<212> TYPE: PRT
<213> ORGANISM: Artificial sequence
<220> FEATURE:
```

```
<223> OTHER INFORMATION: Antigenic peptide

<400> SEQUENCE: 18

Ala Leu Arg Asp Val Gly Glu Arg Ala
1               5

<210> SEQ ID NO 19
<211> LENGTH: 9
<212> TYPE: PRT
<213> ORGANISM: Artificial sequence
<220> FEATURE:
<223> OTHER INFORMATION: Antigenic peptide

<400> SEQUENCE: 19

Ala Leu Arg Asp Val Gly Glu Gly Ala
1               5

<210> SEQ ID NO 20
<211> LENGTH: 9
<212> TYPE: PRT
<213> ORGANISM: Artificial sequence
<220> FEATURE:
<223> OTHER INFORMATION: Antigenic peptide

<400> SEQUENCE: 20

Ala Leu Arg Asp Val Gly Glu Gly Val
1               5

<210> SEQ ID NO 21
<211> LENGTH: 9
<212> TYPE: PRT
<213> ORGANISM: Artificial sequence
<220> FEATURE:
<223> OTHER INFORMATION: Antigenic peptide

<400> SEQUENCE: 21

Ala Leu Arg Asp Glu Glu Glu Gly Ala
1               5

<210> SEQ ID NO 22
<211> LENGTH: 9
<212> TYPE: PRT
<213> ORGANISM: Artificial sequence
<220> FEATURE:
<223> OTHER INFORMATION: Antigenic peptide

<400> SEQUENCE: 22

Ala Leu Arg Asp Glu Glu Glu Gly Val
1               5

<210> SEQ ID NO 23
<211> LENGTH: 9
<212> TYPE: PRT
<213> ORGANISM: Artificial sequence
<220> FEATURE:
<223> OTHER INFORMATION: Antigenic peptide

<400> SEQUENCE: 23

Ala Leu Arg Asp Glu Gly Glu Arg Val
1               5

<210> SEQ ID NO 24
<211> LENGTH: 9
<212> TYPE: PRT
<213> ORGANISM: Artificial sequence
<220> FEATURE:
<223> OTHER INFORMATION: Antigenic peptide
```

```
<400> SEQUENCE: 24

Ala Leu Arg Asp Glu Gly Glu Arg Ala
1               5

<210> SEQ ID NO 25
<211> LENGTH: 9
<212> TYPE: PRT
<213> ORGANISM: Artificial sequence
<220> FEATURE:
<223> OTHER INFORMATION: Antigenic peptide

<400> SEQUENCE: 25

Ala Leu Arg Asp Glu Gly Glu Gly Ala
1               5

<210> SEQ ID NO 26
<211> LENGTH: 9
<212> TYPE: PRT
<213> ORGANISM: Artificial sequence
<220> FEATURE:
<223> OTHER INFORMATION: Antigenic peptide

<400> SEQUENCE: 26

Ala Leu Arg Asp Glu Gly Glu Gly Val
1               5

<210> SEQ ID NO 27
<211> LENGTH: 9
<212> TYPE: PRT
<213> ORGANISM: Artificial sequence
<220> FEATURE:
<223> OTHER INFORMATION: Antigenic peptide

<400> SEQUENCE: 27

Ala Leu Arg Glu Val Glu Glu Arg Val
1               5

<210> SEQ ID NO 28
<211> LENGTH: 9
<212> TYPE: PRT
<213> ORGANISM: Artificial sequence
<220> FEATURE:
<223> OTHER INFORMATION: Antigenic peptide

<400> SEQUENCE: 28

Ala Leu Arg Glu Val Glu Glu Arg Ala
1               5

<210> SEQ ID NO 29
<211> LENGTH: 9
<212> TYPE: PRT
<213> ORGANISM: Artificial sequence
<220> FEATURE:
<223> OTHER INFORMATION: Antigenic peptide

<400> SEQUENCE: 29

Ala Leu Arg Glu Val Glu Glu Gly Ala
1               5

<210> SEQ ID NO 30
<211> LENGTH: 9
<212> TYPE: PRT
<213> ORGANISM: Artificial sequence
<220> FEATURE:
<223> OTHER INFORMATION: Antigenic peptide
```

```
<400> SEQUENCE: 30

Ala Leu Arg Glu Val Glu Glu Gly Val
1               5

<210> SEQ ID NO 31
<211> LENGTH: 9
<212> TYPE: PRT
<213> ORGANISM: Artificial sequence
<220> FEATURE:
<223> OTHER INFORMATION: Antigenic peptide

<400> SEQUENCE: 31

Ala Leu Arg Glu Val Glu Glu Gly Val
1               5

<210> SEQ ID NO 32
<211> LENGTH: 9
<212> TYPE: PRT
<213> ORGANISM: Artificial sequence
<220> FEATURE:
<223> OTHER INFORMATION: Antigenic peptide

<400> SEQUENCE: 32

Ala Leu Arg Glu Val Gly Glu Arg Ala
1               5

<210> SEQ ID NO 33
<211> LENGTH: 9
<212> TYPE: PRT
<213> ORGANISM: Artificial sequence
<220> FEATURE:
<223> OTHER INFORMATION: Antigenic peptide

<400> SEQUENCE: 33

Ala Leu Arg Glu Val Gly Glu Gly Ala
1               5

<210> SEQ ID NO 34
<211> LENGTH: 9
<212> TYPE: PRT
<213> ORGANISM: Artificial sequence
<220> FEATURE:
<223> OTHER INFORMATION: Antigenic peptide

<400> SEQUENCE: 34

Ala Leu Arg Glu Val Gly Glu Gly Val
1               5

<210> SEQ ID NO 35
<211> LENGTH: 9
<212> TYPE: PRT
<213> ORGANISM: Artificial sequence
<220> FEATURE:
<223> OTHER INFORMATION: Antigenic peptide

<400> SEQUENCE: 35

Ala Leu Arg Glu Glu Glu Glu Arg Val
1               5

<210> SEQ ID NO 36
<211> LENGTH: 9
<212> TYPE: PRT
<213> ORGANISM: Artificial sequence
<220> FEATURE:
<223> OTHER INFORMATION: Antigenic peptide

<400> SEQUENCE: 36
```

```
Ala Leu Arg Glu Glu Glu Glu Arg Ala
1               5
```

<210> SEQ ID NO 37
<211> LENGTH: 9
<212> TYPE: PRT
<213> ORGANISM: Artificial sequence
<220> FEATURE:
<223> OTHER INFORMATION: Antigenic peptide

<400> SEQUENCE: 37

```
Ala Leu Arg Glu Glu Glu Glu Gly Ala
1               5
```

<210> SEQ ID NO 38
<211> LENGTH: 9
<212> TYPE: PRT
<213> ORGANISM: Artificial sequence
<220> FEATURE:
<223> OTHER INFORMATION: Antigenic peptide

<400> SEQUENCE: 38

```
Ala Leu Arg Glu Glu Glu Glu Gly Val
1               5
```

<210> SEQ ID NO 39
<211> LENGTH: 9
<212> TYPE: PRT
<213> ORGANISM: Artificial sequence
<220> FEATURE:
<223> OTHER INFORMATION: Antigenic peptide

<400> SEQUENCE: 39

```
Ala Leu Arg Glu Glu Gly Glu Ala Val
1               5
```

<210> SEQ ID NO 40
<211> LENGTH: 9
<212> TYPE: PRT
<213> ORGANISM: Artificial sequence
<220> FEATURE:
<223> OTHER INFORMATION: Antigenic peptide

<400> SEQUENCE: 40

```
Ala Leu Arg Glu Glu Gly Glu Arg Ala
1               5
```

<210> SEQ ID NO 41
<211> LENGTH: 9
<212> TYPE: PRT
<213> ORGANISM: Artificial sequence
<220> FEATURE:
<223> OTHER INFORMATION: Antigenic peptide

<400> SEQUENCE: 41

```
Ala Leu Arg Glu Glu Gly Glu Gly Ala
1               5
```

<210> SEQ ID NO 42
<211> LENGTH: 9
<212> TYPE: PRT
<213> ORGANISM: Artificial sequence
<220> FEATURE:
<223> OTHER INFORMATION: Antigenic peptide

<400> SEQUENCE: 42

```
Ala Leu Lys Asp Val Glu Glu Gly Ala
1               5

<210> SEQ ID NO 43
<211> LENGTH: 9
<212> TYPE: PRT
<213> ORGANISM: Artificial sequence
<220> FEATURE:
<223> OTHER INFORMATION: Antigenic peptide

<400> SEQUENCE: 43

Ala Leu Lys Asp Val Glu Glu Gly Val
1               5

<210> SEQ ID NO 44
<211> LENGTH: 9
<212> TYPE: PRT
<213> ORGANISM: Artificial sequence
<220> FEATURE:
<223> OTHER INFORMATION: Antigenic peptide

<400> SEQUENCE: 44

Ala Leu Lys Asp Val Gly Glu Ala Val
1               5

<210> SEQ ID NO 45
<211> LENGTH: 9
<212> TYPE: PRT
<213> ORGANISM: Artificial sequence
<220> FEATURE:
<223> OTHER INFORMATION: Antigenic peptide

<400> SEQUENCE: 45

Ala Leu Lys Asp Val Gly Glu Arg Ala
1               5

<210> SEQ ID NO 46
<211> LENGTH: 9
<212> TYPE: PRT
<213> ORGANISM: Artificial sequence
<220> FEATURE:
<223> OTHER INFORMATION: Antigenic peptide

<400> SEQUENCE: 46

Ala Leu Lys Asp Val Gly Glu Gly Ala
1               5

<210> SEQ ID NO 47
<211> LENGTH: 9
<212> TYPE: PRT
<213> ORGANISM: Artificial sequence
<220> FEATURE:
<223> OTHER INFORMATION: Antigenic peptide

<400> SEQUENCE: 47

Ala Leu Lys Asp Val Gly Glu Gly Val
1               5

<210> SEQ ID NO 48
<211> LENGTH: 9
<212> TYPE: PRT
<213> ORGANISM: Artificial sequence
<220> FEATURE:
<223> OTHER INFORMATION: Antigenic peptide

<400> SEQUENCE: 48

Ala Leu Lys Asp Glu Glu Glu Arg Val
```

```
<210> SEQ ID NO 49
<211> LENGTH: 9
<212> TYPE: PRT
<213> ORGANISM: Artificial sequence
<220> FEATURE:
<223> OTHER INFORMATION: Antigenic peptide

<400> SEQUENCE: 49

Ala Leu Lys Asp Glu Glu Glu Gly Ala
1               5

<210> SEQ ID NO 50
<211> LENGTH: 9
<212> TYPE: PRT
<213> ORGANISM: Artificial sequence
<220> FEATURE:
<223> OTHER INFORMATION: Antigenic peptide

<400> SEQUENCE: 50

Ala Leu Lys Asp Glu Glu Glu Gly Val
1               5

<210> SEQ ID NO 51
<211> LENGTH: 9
<212> TYPE: PRT
<213> ORGANISM: Artificial sequence
<220> FEATURE:
<223> OTHER INFORMATION: Antigenic peptide

<400> SEQUENCE: 51

Ala Glu Lys Asp Glu Gly Glu Arg Val
1               5

<210> SEQ ID NO 52
<211> LENGTH: 9
<212> TYPE: PRT
<213> ORGANISM: Artificial sequence
<220> FEATURE:
<223> OTHER INFORMATION: Antigenic peptide

<400> SEQUENCE: 52

Ala Leu Lys Asp Glu Gly Glu Arg Ala
1               5

<210> SEQ ID NO 53
<211> LENGTH: 9
<212> TYPE: PRT
<213> ORGANISM: Artificial sequence
<220> FEATURE:
<223> OTHER INFORMATION: Antigenic peptide

<400> SEQUENCE: 53

Ala Leu Lys Asp Glu Gly Glu Gly Ala
1               5

<210> SEQ ID NO 54
<211> LENGTH: 9
<212> TYPE: PRT
<213> ORGANISM: Artificial sequence
<220> FEATURE:
<223> OTHER INFORMATION: Antigenic peptide

<400> SEQUENCE: 54

Ala Leu Lys Asp Glu Gly Glu Gly Val
1               5
```

```
<210> SEQ ID NO 55
<211> LENGTH: 11
<212> TYPE: PRT
<213> ORGANISM: Artificial sequence
<220> FEATURE:
<223> OTHER INFORMATION: Antigenic peptide

<400> SEQUENCE: 55

Ala Leu Lys Glu Val Glu Glu Arg Val Ala Asn
1               5                   10

<210> SEQ ID NO 56
<211> LENGTH: 9
<212> TYPE: PRT
<213> ORGANISM: Artificial sequence
<220> FEATURE:
<223> OTHER INFORMATION: Antigenic peptide

<400> SEQUENCE: 56

Ala Leu Lys Glu Val Glu Glu Arg Ala
1               5

<210> SEQ ID NO 57
<211> LENGTH: 9
<212> TYPE: PRT
<213> ORGANISM: Artificial sequence
<220> FEATURE:
<223> OTHER INFORMATION: Antigenic peptide

<400> SEQUENCE: 57

Ala Leu Lys Glu Val Glu Glu Gly Ala
1               5

<210> SEQ ID NO 58
<211> LENGTH: 9
<212> TYPE: PRT
<213> ORGANISM: Artificial sequence
<220> FEATURE:
<223> OTHER INFORMATION: Antigenic peptide

<400> SEQUENCE: 58

Ala Leu Lys Glu Val Glu Glu Gly Val
1               5

<210> SEQ ID NO 59
<211> LENGTH: 9
<212> TYPE: PRT
<213> ORGANISM: Artificial sequence
<220> FEATURE:
<223> OTHER INFORMATION: Antigenic peptide

<400> SEQUENCE: 59

Ala Leu Lys Glu Val Gly Glu Arg Val
1               5

<210> SEQ ID NO 60
<211> LENGTH: 9
<212> TYPE: PRT
<213> ORGANISM: Artificial sequence
<220> FEATURE:
<223> OTHER INFORMATION: Antigenic peptide

<400> SEQUENCE: 60

Ala Leu Lys Glu Val Gly Glu Arg Ala
1               5
```

```
<210> SEQ ID NO 61
<211> LENGTH: 9
<212> TYPE: PRT
<213> ORGANISM: Artificial sequence
<220> FEATURE:
<223> OTHER INFORMATION: Antigenic peptide

<400> SEQUENCE: 61

Ala Leu Lys Glu Val Gly Glu Gly Ala
1               5

<210> SEQ ID NO 62
<211> LENGTH: 9
<212> TYPE: PRT
<213> ORGANISM: Artificial sequence
<220> FEATURE:
<223> OTHER INFORMATION: Antigenic peptide

<400> SEQUENCE: 62

Ala Leu Lys Glu Val Gly Glu Gly Val
1               5

<210> SEQ ID NO 63
<211> LENGTH: 9
<212> TYPE: PRT
<213> ORGANISM: Artificial sequence
<220> FEATURE:
<223> OTHER INFORMATION: Antigenic peptide

<400> SEQUENCE: 63

Ala Leu Lys Glu Glu Glu Glu Arg Val
1               5

<210> SEQ ID NO 64
<211> LENGTH: 9
<212> TYPE: PRT
<213> ORGANISM: Artificial sequence
<220> FEATURE:
<223> OTHER INFORMATION: Antigenic peptide

<400> SEQUENCE: 64

Ala Leu Lys Glu Glu Glu Glu Arg Ala
1               5

<210> SEQ ID NO 65
<211> LENGTH: 9
<212> TYPE: PRT
<213> ORGANISM: Artificial sequence
<220> FEATURE:
<223> OTHER INFORMATION: Antigenic peptide

<400> SEQUENCE: 65

Ala Leu Lys Glu Glu Glu Glu Gly Ala
1               5

<210> SEQ ID NO 66
<211> LENGTH: 9
<212> TYPE: PRT
<213> ORGANISM: Artificial sequence
<220> FEATURE:
<223> OTHER INFORMATION: Antigenic peptide

<400> SEQUENCE: 66

Ala Leu Lys Glu Glu Glu Glu Gly Val
1               5
```

```
<210> SEQ ID NO 67
<211> LENGTH: 9
<212> TYPE: PRT
<213> ORGANISM: Artificial sequence
<220> FEATURE:
<223> OTHER INFORMATION: Antigenic peptide

<400> SEQUENCE: 67

Ala Leu Lys Glu Glu Gly Glu Arg Val
1               5

<210> SEQ ID NO 68
<211> LENGTH: 9
<212> TYPE: PRT
<213> ORGANISM: Artificial sequence
<220> FEATURE:
<223> OTHER INFORMATION: Antigenic peptide

<400> SEQUENCE: 68

Ala Leu Lys Glu Glu Gly Glu Arg Ala
1               5

<210> SEQ ID NO 69
<211> LENGTH: 9
<212> TYPE: PRT
<213> ORGANISM: Artificial sequence
<220> FEATURE:
<223> OTHER INFORMATION: Antigenic peptide

<400> SEQUENCE: 69

Ala Leu Lys Glu Glu Gly Glu Arg Ala
1               5

<210> SEQ ID NO 70
<211> LENGTH: 9
<212> TYPE: PRT
<213> ORGANISM: Artificial sequence
<220> FEATURE:
<223> OTHER INFORMATION: Antigenic peptide

<400> SEQUENCE: 70

Ala Leu Gly Glu Glu Gly Glu Gly Val
1               5

<210> SEQ ID NO 71
<211> LENGTH: 373
<212> TYPE: PRT
<213> ORGANISM: Homo sapiens
<220> FEATURE:
<221> NAME/KEY: MISC_FEATURE
<222> LOCATION: (334)..(334)
<223> OTHER INFORMATION: Xaa at position 334 is Lys in MAGE-C2 and Glu
      in CT-10

<400> SEQUENCE: 71

Met Pro Pro Val Pro Gly Val Pro Phe Arg Asn Val Asp Asn Asp Ser
1               5                   10                  15

Pro Thr Ser Val Glu Leu Glu Asp Trp Val Asp Ala Gln His Pro Thr
                20                  25                  30

Asp Glu Glu Glu Glu Glu Ala Ser Ser Ala Ser Ser Thr Leu Tyr Leu
            35                  40                  45

Val Phe Ser Pro Ser Ser Phe Ser Thr Ser Ser Ser Leu Ile Leu Gly
        50                  55                  60

Gly Pro Glu Glu Glu Glu Val Pro Ser Gly Val Ile Pro Asn Leu Thr
65                  70                  75                  80
```

-continued

```
Glu Ser Ile Pro Ser Ser Pro Gln Gly Pro Pro Gln Gly Pro Ser
                85                  90                  95

Gln Ser Pro Leu Ser Ser Cys Cys Ser Ser Phe Ser Trp Ser Ser Phe
            100                 105                 110

Ser Glu Glu Ser Ser Gln Lys Gly Glu Asp Thr Gly Thr Cys Gln
            115                 120                 125

Gly Leu Pro Asp Ser Glu Ser Ser Phe Thr Tyr Thr Leu Asp Glu Lys
        130                 135                 140

Val Ala Glu Leu Val Glu Phe Leu Leu Leu Lys Tyr Glu Ala Glu Glu
145                 150                 155                 160

Pro Val Thr Glu Ala Glu Met Leu Met Ile Val Lys Tyr Lys Asp
                165                 170                 175

Tyr Phe Pro Val Ile Leu Lys Arg Ala Arg Glu Phe Met Glu Leu Leu
                180                 185                 190

Phe Gly Leu Ala Leu Ile Glu Val Gly Pro Asp His Phe Cys Val Phe
        195                 200                 205

Ala Asn Thr Val Gly Leu Thr Asp Glu Gly Ser Asp Asp Glu Gly Met
    210                 215                 220

Pro Glu Asn Ser Leu Leu Ile Ile Ile Leu Ser Val Ile Phe Ile Lys
225                 230                 235                 240

Gly Asn Cys Ala Ser Glu Glu Val Ile Trp Glu Val Leu Asn Ala Val
                245                 250                 255

Gly Val Tyr Ala Gly Arg Glu His Phe Val Tyr Gly Glu Pro Arg Glu
            260                 265                 270

Leu Leu Thr Lys Val Trp Val Gln Gly His Tyr Leu Glu Tyr Arg Glu
        275                 280                 285

Val Pro His Ser Pro Pro Tyr Tyr Glu Phe Leu Trp Gly Pro Arg
290                 295                 300

Ala His Ser Glu Ser Ile Lys Lys Lys Val Leu Glu Phe Leu Ala Lys
305                 310                 315                 320

Leu Asn Asn Thr Val Pro Ser Ser Phe Pro Ser Trp Tyr Xaa Asp Ala
                325                 330                 335

Leu Lys Asp Val Glu Glu Arg Val Gln Ala Thr Ile Asp Thr Ala Asp
            340                 345                 350

Asp Ala Thr Val Met Ala Ser Glu Ser Leu Ser Val Met Ser Ser Asn
        355                 360                 365

Val Ser Phe Ser Glu
    370
```

<210> SEQ ID NO 72
<211> LENGTH: 1983
<212> TYPE: DNA
<213> ORGANISM: Homo sapiens
<220> FEATURE:
<221> NAME/KEY: MISC_FEATURE
<222> LOCATION: (1329)..(1329)
<223> OTHER INFORMATION: n at position 1329 is a in MAGE-C2 and g in CT10

<400> SEQUENCE: 72

```
tgggaatctg acggatcgga ggcatttgtg aggaggcgcg aatcaagtta gcgggggaa      60 gagtcttaga cctggccagt cctcagggtg agggccctga ggaagaactg agggacctcc    120
caccatagag agaagaaacc ccggcctgta ctgcgctgcc gtgagactgg tgctccagga    180
accaggtggt gacgaactgg gtgtgaggca cacagcctaa agtcagcaca gcagaggagg    240
cccaggcagt gccaggagtc aaggcctgtt ggatctcatc atccatatcc ctgttgatac    300
```

```
gtttacctgc tgctcctgaa gaagtcgtca tgcctcccgt tccaggcgtt ccattccgca      360
acgttgacaa cgactccccg acctcagttg agttagaaga ctgggtagat gcacagcatc      420
ccacagatga ggaagaggag gaagcctcct ccgcctcttc cactttgtac ttagtatttt      480
cccctcttc tttctccaca tcctcttctc tgattcttgg tggtcctgag gaggaggagg       540
tgccctctgg tgtgatacca aatcttaccg agagcattcc cagtagtcct ccacagggtc      600
ctccacaggg tccttcccag agtcctctga gctcctgctg ctcctctttt tcatggagct      660
cattcagtga ggagtccagc agccagaaag gggaggatac aggcacctgt cagggcctgc      720
cagacagtga gtcctctttc acatatacac tagatgaaaa ggtggccgag ttagtggagt      780
tcctgctcct caaatacgaa gcagaggagc ctgtaacaga ggcagagatg ctgatgattg      840
tcatcaagta caaagattac tttcctgtga tactcaagag agcccgtgag ttcatggagc      900
ttcttttgg ccttgccctg atagaagtgg gccctgacca cttctgtgtg tttgcaaaca      960
cagtaggcct caccgatgag ggtagtgatg atgagggcat gcccgagaac agcctcctga     1020
ttattattct gagtgtgatc ttcataaagg gcaactgtgc ctctgaggag gtcatctggg     1080
aagtgctgaa tgcagtaggg gtatatgctg ggagggagca cttcgtctat ggggagccta     1140
gggagctcct cactaaagtt tgggtgcagg acattacct ggagtatcgg gaggtgcccc     1200
acagttctcc tccatattat gaattcctgt ggggtccaag agcccattca gaaagcatca     1260
agaagaaagt actagagttt ttagccaagc tgaacaacac tgttcctagt tcctttccat     1320
cctggtacna ggatgctttg aaagatgtgg aagagagagt ccaggccaca attgataccg     1380
cagatgatgc cactgtcatg gccagtgaaa gcctcagtgt catgtccagc aacgtctcct     1440
tttctgagtg aagtctagga tagttttcttc cccttgtgtt tgaacagggc agtttaggtt     1500
ctaggtagtg gagggccagg tggggctcga ggaacgtagt gttctttgca tttctgtccc     1560
atatgggtga tgtagagatt tacctgtttt tcagtatttt ctaaatgctt ttcctttgaa     1620
tagcaggtag ttagcttcag agtgttaatt tatgaatatt agtcgcacat gtattgctct     1680
ttatctggtt taagagtaac agtttgatat tttgttaaaa aaatggaaat accttctccc     1740
ttattttgtg atctgtaaca gggtagtgtg gtattgtaat aggcattttt ttttttttt      1800
acaatgtgca ataactcagc agttaaatag tggaacaaaa ttgaagggtg gtcagtagtt     1860
tcatttcctt gtcctgctta ttcttttgtt cttgaaaatt atatatacct ggctttgctt     1920
agcttgttga agaaagtagc agaaattaaa tcttaataaa agaaaaaaaa aaaaaaaaa     1980
agg                                                                   1983
```

```
<210> SEQ ID NO 73
<211> LENGTH: 1142
<212> TYPE: PRT
<213> ORGANISM: Homo sapiens

<400> SEQUENCE: 73

Met Gly Asp Lys Asp Met Pro Thr Ala Gly Met Pro Ser Leu Leu Gln
1               5                   10                  15

Ser Ser Ser Glu Ser Pro Gln Ser Cys Pro Glu Gly Glu Asp Ser Gln
            20                  25                  30

Ser Pro Leu Gln Ile Pro Gln Ser Ser Pro Glu Ser Asp Asp Thr Leu
        35                  40                  45

Tyr Pro Leu Gln Ser Pro Gln Ser Arg Ser Glu Gly Glu Asp Ser Ser
    50                  55                  60
```

```
Asp Pro Leu Gln Arg Pro Pro Glu Gly Lys Asp Ser Gln Ser Pro Leu
 65                  70                  75                  80

Gln Ile Pro Gln Ser Ser Pro Glu Gly Asp Asp Thr Gln Ser Pro Leu
                 85                  90                  95

Gln Asn Ser Gln Ser Ser Pro Glu Gly Lys Asp Ser Leu Ser Pro Leu
            100                 105                 110

Gln Ile Ser Gln Ser Pro Pro Glu Gly Glu Asp Val Gln Ser Pro Leu
        115                 120                 125

Gln Asn Pro Ala Ser Ser Phe Phe Ser Ser Ala Leu Leu Ser Ile Phe
130                 135                 140

Gln Ser Ser Pro Glu Ser Ile Gln Ser Pro Phe Glu Gly Phe Pro Gln
145                 150                 155                 160

Ser Val Leu Gln Ile Pro Val Ser Ala Ala Ser Ser Ser Thr Leu Val
                165                 170                 175

Ser Ile Phe Gln Ser Ser Pro Glu Ser Thr Gln Ser Pro Phe Glu Gly
            180                 185                 190

Phe Pro Gln Ser Pro Leu Gln Ile Pro Val Ser Arg Ser Phe Ser Ser
        195                 200                 205

Thr Leu Leu Ser Ile Phe Gln Ser Ser Pro Glu Arg Ser Gln Arg Thr
210                 215                 220

Ser Glu Gly Phe Ala Gln Ser Pro Leu Gln Ile Pro Val Ser Ser Ser
225                 230                 235                 240

Ser Ser Ser Thr Leu Leu Ser Leu Phe Gln Ser Ser Pro Glu Arg Thr
                245                 250                 255

Gln Ser Thr Phe Glu Gly Phe Pro Gln Ser Pro Leu Gln Ile Pro Val
            260                 265                 270

Ser Arg Ser Phe Ser Ser Thr Leu Leu Ser Ile Phe Gln Ser Ser Pro
        275                 280                 285

Glu Arg Thr Gln Ser Thr Phe Glu Gly Phe Ala Gln Ser Pro Leu Gln
290                 295                 300

Ile Pro Val Ser Pro Ser Phe Ser Ser Thr Leu Val Ser Ile Phe Gln
305                 310                 315                 320

Ser Ser Pro Glu Arg Thr Gln Ser Thr Phe Glu Gly Phe Pro Gln Ser
                325                 330                 335

Pro Leu Gln Ile Pro Val Ser Ser Phe Ser Ser Thr Leu Leu Ser
            340                 345                 350

Leu Phe Gln Ser Ser Pro Glu Arg Thr Gln Ser Thr Phe Glu Gly Phe
        355                 360                 365

Pro Gln Ser Pro Leu Gln Ile Pro Gly Ser Pro Ser Phe Ser Ser Thr
370                 375                 380

Leu Leu Ser Leu Phe Gln Ser Pro Glu Arg Thr His Ser Thr Phe
385                 390                 395                 400

Glu Gly Phe Pro Gln Ser Pro Leu Gln Ile Pro Met Thr Ser Ser Phe
                405                 410                 415

Ser Ser Thr Leu Leu Ser Ile Leu Gln Ser Ser Pro Glu Ser Ala Gln
            420                 425                 430

Ser Ala Phe Glu Gly Phe Pro Gln Ser Pro Leu Gln Ile Pro Val Ser
        435                 440                 445

Ser Ser Phe Ser Tyr Thr Leu Leu Ser Leu Phe Gln Ser Ser Pro Glu
        450                 455                 460

Arg Thr His Ser Thr Phe Glu Gly Phe Pro Gln Ser Pro Leu Gln Ile
465                 470                 475                 480

Pro Val Ser Ser Ser Ser Ser Ser Ser Thr Leu Leu Ser Leu Phe Gln
```

```
                485                 490                 495
Ser Ser Pro Glu Cys Thr Gln Ser Thr Phe Glu Gly Phe Pro Gln Ser
            500                 505                 510

Pro Leu Gln Ile Pro Gln Ser Pro Glu Gly Glu Asn Thr His Ser
        515                 520                 525

Pro Leu Gln Ile Val Pro Ser Leu Pro Glu Trp Glu Asp Ser Leu Ser
            530                 535                 540

Pro His Tyr Phe Pro Gln Ser Pro Gln Gly Glu Asp Ser Leu Ser
545                 550                 555                 560

Pro His Tyr Phe Gln Ser Pro Gln Gly Glu Asp Ser Leu Ser
            565                 570                 575

Pro His Tyr Phe Pro Gln Ser Pro Gln Gly Glu Asp Ser Leu Ser Pro
            580                 585                 590

His Tyr Phe Pro Gln Ser Pro Pro Gln Gly Glu Asp Ser Met Ser Pro
        595                 600                 605

Leu Tyr Phe Pro Gln Ser Pro Leu Gln Gly Glu Glu Phe Gln Ser Ser
        610                 615                 620

Leu Gln Ser Pro Val Ser Ile Cys Ser Ser Ser Thr Pro Ser Ser Leu
625                 630                 635                 640

Pro Gln Ser Phe Pro Glu Ser Ser Gln Ser Pro Pro Glu Gly Pro Val
                645                 650                 655

Gln Ser Pro Leu His Ser Pro Gln Ser Pro Pro Glu Gly Met His Ser
                660                 665                 670

Gln Ser Pro Leu Gln Ser Pro Glu Ser Ala Pro Glu Gly Glu Asp Ser
            675                 680                 685

Leu Ser Pro Leu Gln Ile Pro Gln Ser Pro Leu Glu Gly Glu Asp Ser
        690                 695                 700

Leu Ser Ser Leu His Phe Pro Gln Ser Pro Glu Trp Glu Asp Ser
705                 710                 715                 720

Leu Ser Pro Leu His Phe Pro Gln Phe Pro Gln Gly Glu Asp Phe
                725                 730                 735

Gln Ser Ser Leu Gln Ser Pro Val Ser Ile Cys Ser Ser Ser Thr Ser
                740                 745                 750

Leu Ser Leu Pro Gln Ser Phe Pro Glu Ser Pro Gln Ser Pro Pro Glu
        755                 760                 765

Gly Pro Ala Gln Ser Pro Leu Gln Arg Pro Val Ser Ser Phe Phe Ser
        770                 775                 780

Tyr Thr Leu Ala Ser Leu Leu Gln Ser Ser His Glu Ser Pro Gln Ser
785                 790                 795                 800

Pro Pro Glu Gly Pro Ala Gln Ser Pro Leu Gln Ser Pro Val Ser Ser
                805                 810                 815

Phe Pro Ser Ser Thr Ser Ser Leu Ser Gln Ser Ser Pro Val Ser
            820                 825                 830

Ser Phe Pro Ser Ser Thr Ser Ser Leu Ser Lys Ser Ser Pro Glu
        835                 840                 845

Ser Pro Leu Gln Ser Pro Val Ile Ser Phe Ser Ser Thr Ser Leu
        850                 855                 860

Ser Pro Phe Ser Glu Glu Ser Ser Pro Val Asp Glu Tyr Thr Ser
865                 870                 875                 880

Ser Ser Asp Thr Leu Leu Glu Ser Asp Ser Leu Thr Asp Ser Glu Ser
                885                 890                 895

Leu Ile Glu Ser Glu Pro Leu Phe Thr Tyr Thr Leu Asp Glu Lys Val
                900                 905                 910
```

```
Asp Glu Leu Ala Arg Phe Leu Leu Leu Lys Tyr Gln Val Lys Gln Pro
        915                 920                 925

Ile Thr Lys Ala Glu Met Leu Thr Asn Val Ile Ser Arg Tyr Thr Gly
        930                 935                 940

Tyr Phe Pro Val Ile Phe Arg Lys Ala Arg Glu Phe Ile Glu Ile Leu
945                 950                 955                 960

Phe Gly Ile Ser Leu Arg Glu Val Asp Pro Asp Ser Tyr Val Phe
                965                 970                 975

Val Asn Thr Leu Asp Leu Thr Ser Glu Gly Cys Leu Ser Asp Glu Gln
            980                 985                 990

Gly Met Ser Gln Asn Arg Leu Leu  Ile Leu Ile Leu Ser  Ile Ile Phe
        995                 1000                1005

Ile Lys  Gly Thr Tyr Ala Ser  Glu Glu Val Ile Trp  Asp Val Leu
    1010                1015                1020

Ser Gly  Ile Gly Val Arg Ala  Gly Arg Glu His Phe  Ala Phe Gly
    1025                1030                1035

Glu Pro  Arg Glu Leu Leu Thr  Lys Val Trp Val Gln  Glu His Tyr
    1040                1045                1050

Leu Glu  Tyr Arg Glu Val Pro  Asn Ser Ser Pro Pro  Arg Tyr Glu
    1055                1060                1065

Phe Leu  Trp Gly Pro Arg Ala  His Ser Glu Val Ile  Lys Arg Lys
    1070                1075                1080

Val Val  Glu Phe Leu Ala Met  Leu Lys Asn Thr Val  Pro Ile Thr
    1085                1090                1095

Phe Pro  Ser Ser Tyr Lys Asp  Ala Leu Lys Asp Val  Glu Glu Arg
    1100                1105                1110

Ala Gln  Ala Ile Ile Asp Thr  Thr Asp Asp Ser Thr  Ala Thr Glu
    1115                1120                1125

Ser Ala  Ser Ser Ser Val Met  Ser Pro Ser Phe Ser  Ser Glu
    1130                1135                1140

<210> SEQ ID NO 74
<211> LENGTH: 4265
<212> TYPE: DNA
<213> ORGANISM: Homo sapiens

<400> SEQUENCE: 74
gtctgaagga cctgaggcat tttgtgacga ggatcgtctc aggtcagcgg agggaggaga     60
cttatagacc tatccagtct tcaaggtgct ccagaaagca ggagttgaag acctgggtgt    120
gagggacaca tacatcctaa aagcaccaca gcagaggagg cccaggcagt gccaggagtc    180
aaggttccca gaagacaaac cccctaggaa gacaggcgac ctgtgaggcc ctagagcacc    240
accttaagag aagaagagct gtaagccggc ctttgtcaga gccatcatgg gggacaagga    300
tatgcctact gctgggatgc cgagtcttct ccagagttcc tctgagagtc ctcagagttg    360
tcctgagggg gaggactccc agtctcctct ccagattccc agagttctc tgagagcga     420 cgacaccctg tatcctctcc agagtcctca gagtcgttct gaggggagg actcctcgga    480 tcctctccag agacctcctg aggggaagga ctcccagtct cctctccaga ttccccagag    540
ttctcctgag ggcgacgaca cccagtctcc tctccagaat tctcagagtt ctcctgaggg    600
gaaggactcc ctgtctcctc tagagatttc tcagagccct cctgagggtg aggatgtcca    660
gtctcctctg cagaatcctg cgagttcctt cttctcctct gctttattga gtattttcca    720
gagttcccct gagagtattc aaagtccttt tgagggtttt ccccagtctg ttctccagat    780
```

```
tcctgtgagc gccgcctcct cctccacttt agtgagtatt ttccagagtt cccctgagag    840
tactcaaagt ccttttgagg gttttcccca gtctccactc cagattcctg tgagccgctc    900
cttctcctcc actttattga gtattttcca gagttcccct gagagaagtc agagaacttc    960
tgagggtttt gcacagtctc ctctccagat tcctgtgagc tcctcctcgt cctccacttt   1020
actgagtctt ttccagagtt cccctgagag aactcagagt acttttgagg gttttcccca   1080
gtctccactc cagattcctg tgagccgctc cttctcctcc actttattga gtattttcca   1140
gagttcccct gagagaactc agagtacttt tgagggtttt gcccagtctc ctctccagat   1200
tcctgtgagc ccctccttct cctccacttt agtgagtatt ttccagagtt cccctgagag   1260
aactcagagt acttttgagg gttttcccca gtcctctctc cagattcctg tgagctcctc   1320
cttctcctcc actttattga gtcttttcca gagttcccct gagagaactc agagtacttt   1380
tgagggtttt cccagtctc ctctccagat tcctggaagc ccctccttct cctccacttt   1440
actgagtctt ttccagagtt cccctgagag aactcacagt acttttgagg gttttcccca   1500
gtctcctctc cagattccta tgacctcctc cttctcctct actttattga gtattttaca   1560
gagttctcct gagagtgctc aaagtgcttt tgagggtttt cccagtctc ctctccagat   1620
tcctgtgagc tcctctttct cctacacttt attgagtctt ttccagagtt cccctgagag   1680
aactcacagt acttttgagg gttttcccca gtcctctctc cagattcctg tgagctcctc   1740
ctcctcctcc tccactttat tgagtctttt ccagagttcc cctgagtgta ctcaaagtac   1800
ttttgagggt ttccccagt ctcctctcca gattcctcag agtcctcctg aaggggagaa   1860
tacccattct cctctccaga ttgttccaag tcttcctgag tgggaggact ccctgtctcc   1920
tcactacttt cctcagagcc ctcctcaggg ggaggactcc ctatctcctc actactttcc   1980
tcagagccct cctcaggggg aggactcccc gtctcctcac tacttcctc agagccctca   2040
ggggagggac tccctgtctc tcactactt tcctcagagc cctcctcagg gggaggactc   2100
catgtctcct ctctactttc ctcagagtcc tcttcagggg gaggaattcc agtcttctct   2160
ccagagccct gtgagcatct gctcctcctc cactccatcc agtcttcccc agagtttccc   2220
tgagagttct cagagtcctc ctgaggggcc tgtccagtct cctctccata gtcctcagag   2280
ccctcctgag gggatgcact cccaatctcc tctccagagt cctgagagtg ctcctgaggg   2340
ggaggattcc ctgtctcctc tccaaattcc tcagagtcct cttgagggag aggactccct   2400
gtcttctctc catttttcctc agagtcctcc tgagtgggag gactccctct cctctccca   2460
ctttcctcag tttcctcctc aggggagga cttccagtct tctctccaga gtcctgtgag   2520
tatctgctcc tcctccactt cttttgagtct tccccagagt ttccctgaga gtcctcagag   2580
tcctcctgag gggcctgctc agtctcctct ccagagacct gtcagctcct tcttctccta   2640
cactttagcg agtcttctcc aaagttccca tgagagtcct cagagtcctc ctgaggggcc   2700
tgcccagtct cctctccaga gtcctgtgag ctccttcccc tcctccactt catcgagtct   2760
ttccagagt tctcctgtga gctccttccc ctcctccact tcatcgagtc tttccaagag   2820
ttcccctgag agtcctctcc agagtcctgt gatctccttc tcctcctcca cttcattgag   2880
cccattcagt gaaagtcca gcagcccagt agatgaatat acaagttcct cagacacctt   2940
gctagagagt gattccttga cagacagcga gtccttgata gagagcgagc ccttgttcac   3000
ttatacactg gatgaaaagg tggacgagtt ggcgcggttt cttctcctca aatatcaagt   3060
gaagcagcct atcacaaagg cagagatgct gacgaatgtc atcagcaggt acacgggcta   3120
```

-continued

```
ctttcctgtg atcttcagga aagcccgtga gttcatagag atacttttg gcatttccct    3180 gagagaagtg gaccctgatg actcctatgt ctttgtaaac acattagacc tcacctctga    3240
ggggtgtctg agtgatgagc agggcatgtc ccagaaccgc ctcctgattc ttattctgag    3300
tatcatcttc ataaagggca cctatgcctc tgaggaggtc atctgggatg tgctgagtgg    3360 aatagggggtg cgtgctggga gggagcactt tgcctttggg gagcccaggg agctcctcac    3420
taaagtttgg gtgcaggaac attacctaga gtaccgggag gtgcccaact cttctcctcc    3480
tcgttacgaa ttcctgtggg gtccaagagc tcattcagaa gtcattaaga ggaaagtagt    3540
agagtttttg gccatgctaa agaataccgt ccctattacc tttccatcct cttacaagga    3600
tgctttgaaa gatgtggaag agagagccca ggccataatt gacaccacag atgattcgac    3660
tgccacagaa agtgcaagct ccagtgtcat gtcccccagc ttctcttctg agtgaagtct    3720
agggcagatt cttccctctg agtttgaagg gggcagtcga gtttctacgt ggtggagggc    3780
ctggttgagg ctggagagaa cacagtgcta tttgcatttc tgttccatat gggtagttat    3840
ggggtttacc tgttttactt ttgggtattt ttcaaatgct tttcctatta ataacaggtt    3900
taaatagctt cagaatccta gtttatgcac atgagtcgca catgtattgc tgttttttctg    3960 gtttaagagt aacagtttga tattttgtaa aaacaaaaac acccaaac acaccacatt    4020 gggaaaacct tctgcctcat tttgtgatgt gtcacaggtt aatgtggtgt tactgtagga    4080
attttcttga aactgtgaag gaactctgca gttaaatagt ggaataaagt aaaggattgt    4140
taatgtttgc atttcctcag gtcctttagt ctgttgttct tgaaaactaa agatacatac    4200
ctggtttgct tggcttacgt aagaaagtcg aagaaagtaa actgtaataa ataaaagtgt    4260
cagtg                                                                4265
```

<210> SEQ ID NO 75
<211> LENGTH: 77
<212> TYPE: DNA
<213> ORGANISM: Homo sapiens

<400> SEQUENCE: 75

```
gttcccagca gacaaactcc ctaggaagac aggagacctg tgaggcccta gagcaccacc      60
ttaagagaag aagagct                                                    77
```

<210> SEQ ID NO 76
<211> LENGTH: 2887
<212> TYPE: DNA
<213> ORGANISM: Homo sapiens
<220> FEATURE:
<221> NAME/KEY: MISC_FEATURE
<222> LOCATION: (1)..(2887)
<223> OTHER INFORMATION: MAGE-C2 gene

<400> SEQUENCE: 76

```
tgggaatctg acgatcgga ggcatttgtg aggaggcgcg aatcaagtta gcgggggggaa      60 gagtcttaga cctggccagt cctcagggtg agggccctga ggaagaactg agggacctcc     120
caccatagag agaagaaacc ccggcctgta ctgcgctgcc gtgagactgg taggtcccag     180
acagggaaat ggccccagaa gaagggagga ggtgccggcc ctctagggaa taaataggaa     240
gacactgagg agggctgggg ggaacgcccc acctcagagg gcagattccc agagattccc     300
accctgctcc tcaagtatca gccctcgtag agctccccag tcagctcagg cggggtggca     360
gccatcttat tcctgggtga gtggcgtagg ggaggcggag gccttggtct gagggtccca     420
tggcaagtca gcacggggag ctgcctctgg ttggcagagg gaagattccc aggccctgct     480
```

```
ggggataaga ctgaggagtc acatgtgcat cagaacggac gtgaggctac cccgactgcc    540
cccatggtag agtgctggga ggtggctgcc accgccctac ctcccactgc tctcagggat    600
gtggcggttg ctctgaggtt ttgccttagg ccagcagagt ggtggaggct cggccctctc    660
tgagaagccg tgaagttgct aattaaattc tgaggggggcc atgcagtcca gaactatgag    720
gctctgggat tctggccagc cccagctgtc agccctagca ggcccaagac cctacttgca    780
gtctttagcc tgagggctc cctcacttcc tcttgcaggt gctccaggaa ccaggtggtg    840
acgaactggg tgtgaggcac acagcctaaa gtcagcacag cagaggaggc caggcagtg    900 ccaggagtca aggtgagtgc acaccctggc tgtgtaccaa gggccctacc cccagaaaca    960
gaggagaccc cacagcaccc ggccctaccc acctattgtc actcctgggg tctcaggctc   1020
tgcctgccag ctgtgccctg aggtgtgttc ccacatcctc ctacaggttc ccagcagaca   1080
aactccctag gaagacagga gacctgtgag gccctagagc accaccttaa gagaagaaga   1140
gctgtaaggt ggcctttgtc agagccatca tgggtgagtt tctcagctga ggccactcac   1200
actgtcactc tcttccacag gcctgttgga tctcatcatc catatccctg ttgatacgtt   1260
tacctgctgc tcctgaagaa gtcgtcatgc ctcccgttcc aggcgttcca ttccgcaacg   1320
ttgacaacga ctccccgacc tcagttgagt tagaagactg ggtagatgca cagcatccca   1380
cagatgagga agaggaggaa gcctcctccg cctcttccac tttgtactta gtattttccc   1440
cctcttcttt ctccacatcc tcttctctga ttcttggtgg tcctgaggag gaggaggtgc   1500
cctctggtgt gataccaaat cttaccgaga gcattcccag tagtcctcca cagggtcctc   1560
cacagggtcc ttcccagagt cctctgagct cctgctgctc ctcttttca tggagctcat   1620 tcagtgagga gtccagcagc cagaaagggg aggatacagg cacctgtcag ggcctgccag   1680
acagtgagtc ctctttcaca tatacactag atgaaaaggt ggccgagtta gtggagttcc   1740
tgctcctcaa atacgaagca gaggagcctg taacagaggc agagatgctg atgattgtca   1800
tcaagtacaa agattacttt cctgtgatac tcaagagagc ccgtgagttc atggagcttc   1860 ttttttggcct tgccctgata gaagtgggcc ctgaccactt ctgtgtgttt gcaaacacag   1920
taggcctcac cgatgagggt agtgatgatg agggcatgcc cgagaacagc ctcctgatta   1980
ttattctgag tgtgatcttc ataaagggca actgtgcctc tgaggaggtc atctgggaag   2040
tgctgaatgc agtaggggta tatgctggga gggagcactt cgtctatggg gagcctaggg   2100
agctcctcac taaagtttgg gtgcaggac attacctgga gtatcgggag gtgccccaca   2160
gttctcctcc atattatgaa ttcctgtggg gtccaagagc ccattcagaa agcatcaaga   2220
agaaagtact agagttttta gccaagctga caaacactgt tcctagttcc tttccatcct   2280
ggtacaagga tgctttgaaa gatgtggaag agagagtcca ggccacaatt gataccgcag   2340
atgatgccac tgtcatggcc agtgaaagcc tcagtgtcat gtccagcaac gtctcctttt   2400
ctgagtgaag tctaggatag tttcttcccc ttgtgtttga acagggcagt ttaggttcta   2460
ggtagtggag ggccaggtgg ggctcgagga acgtagtgtt cttgcatttt ctgtcccata   2520
tgggtgatgt agagatttac ctgttttca gtattttcta aatgctttc ctttgaatag   2580 caggtagtta gcttcagagt gttaatttat gaatattagt cgcacatgta ttgctcttta   2640
tctggtttaa gagtaacagt ttgatatttt gttaaaaaaa tggaaatacc ttctcccta   2700 ttttgtgatc tgtaacaggg tagtgtggta ttgtaatagg catttttttt tttttttaca   2760
atgtgcaata actcagcagt taaatagtgg aacaaaattg aagggtggtc agtagtttca   2820
```

```
tttccttgtc ctgcttattc ttttgttctt gaaaattata tatacctggc tttgcttagc    2880
ttgttga                                                              2887
```

<210> SEQ ID NO 77
<211> LENGTH: 10
<212> TYPE: PRT
<213> ORGANISM: Homo sapiens

<400> SEQUENCE: 77

```
Leu Leu Phe Gly Leu Ala Leu Ile Glu Val
1               5                   10
```

<210> SEQ ID NO 78
<211> LENGTH: 9
<212> TYPE: PRT
<213> ORGANISM: Homo sapiens

<400> SEQUENCE: 78

```
Leu Phe Gly Leu Ala Leu Ile Glu Val
1               5
```

<210> SEQ ID NO 79
<211> LENGTH: 9
<212> TYPE: PRT
<213> ORGANISM: Homo sapiens

<400> SEQUENCE: 79

```
Leu Leu Phe Gly Leu Ala Leu Ile Glu
1               5
```

<210> SEQ ID NO 80
<211> LENGTH: 8
<212> TYPE: PRT
<213> ORGANISM: Homo sapiens

<400> SEQUENCE: 80

```
Leu Leu Phe Gly Leu Ala Leu Ile
1               5
```

<210> SEQ ID NO 81
<211> LENGTH: 16
<212> TYPE: PRT
<213> ORGANISM: Artificial sequence
<220> FEATURE:
<223> OTHER INFORMATION: Protein sequence of minigene 14 Figure 12B

<400> SEQUENCE: 81

```
Met Glu Leu Leu Phe Gly Leu Ala Leu Ile Glu Val Gly Pro Asp His
1               5                   10                  15
```

<210> SEQ ID NO 82
<211> LENGTH: 10
<212> TYPE: PRT
<213> ORGANISM: Homo sapiens

<400> SEQUENCE: 82

```
Ile Leu Phe Gly Ile Ser Leu Arg Glu Val
1               5                   10
```

<210> SEQ ID NO 83
<211> LENGTH: 10
<212> TYPE: PRT
<213> ORGANISM: Homo sapiens

<400> SEQUENCE: 83
```

```
Leu Val Phe Gly Ile Asp Val Lys Glu Val
1               5                   10

<210> SEQ ID NO 84
<211> LENGTH: 10
<212> TYPE: PRT
<213> ORGANISM: Homo sapiens

<400> SEQUENCE: 84

Leu Ile Phe Gly Ile Ala Leu Thr Asp Met
1               5                   10

<210> SEQ ID NO 85
<211> LENGTH: 10
<212> TYPE: PRT
<213> ORGANISM: Homo sapiens

<400> SEQUENCE: 85

Leu Val Phe Gly Leu Ala Leu Lys Glu Val
1               5                   10

<210> SEQ ID NO 86
<211> LENGTH: 10
<212> TYPE: PRT
<213> ORGANISM: Homo sapiens

<400> SEQUENCE: 86

Leu Leu Phe Gly Ile Asp Val Lys Glu Val
1               5                   10

<210> SEQ ID NO 87
<211> LENGTH: 10
<212> TYPE: PRT
<213> ORGANISM: Homo sapiens

<400> SEQUENCE: 87

Val Val Phe Gly Leu Glu Leu Asn Lys Val
1               5                   10

<210> SEQ ID NO 88
<211> LENGTH: 10
<212> TYPE: PRT
<213> ORGANISM: Homo sapiens
<220> FEATURE:
<221> NAME/KEY: MISCH_FEATURE
<222> LOCATION: (1)..(1)
<223> OTHER INFORMATION: Xaa may be any amino acid

<400> SEQUENCE: 88

Xaa Leu Phe Gly Leu Ala Leu Ile Glu Val
1               5                   10

<210> SEQ ID NO 89
<211> LENGTH: 8
<212> TYPE: PRT
<213> ORGANISM: Homo sapiens

<400> SEQUENCE: 89

Ala Ser Ser Thr Leu Tyr Leu Val
1               5

<210> SEQ ID NO 90
<211> LENGTH: 9
<212> TYPE: PRT
<213> ORGANISM: Homo sapiens
```

```
<400> SEQUENCE: 90

Ser Ala Ser Ser Thr Leu Tyr Val Phe
1               5

<210> SEQ ID NO 91
<211> LENGTH: 8
<212> TYPE: PRT
<213> ORGANISM: Homo sapiens

<400> SEQUENCE: 91

Ser Ser Thr Leu Tyr Leu Val Phe
1               5

<210> SEQ ID NO 92
<211> LENGTH: 8
<212> TYPE: PRT
<213> ORGANISM: Homo sapiens

<400> SEQUENCE: 92

Ala Ser Ser Thr Leu Tyr Leu Val
1               5

<210> SEQ ID NO 93
<211> LENGTH: 60
<212> TYPE: DNA
<213> ORGANISM: Artificial sequence
<220> FEATURE:
<223> OTHER INFORMATION: OligodT(T7) primer

<400> SEQUENCE: 93
tctagtcgac ggccagtgaa ttgtaatacg actcactata gggcgttttt tttttttttt    60

<210> SEQ ID NO 94
<211> LENGTH: 22
<212> TYPE: DNA
<213> ORGANISM: Homo sapiens

<400> SEQUENCE: 94
gtgagacaca ggttacgaat gt                                             22

<210> SEQ ID NO 95
<211> LENGTH: 24
<212> TYPE: DNA
<213> ORGANISM: Homo sapiens

<400> SEQUENCE: 95
tctggatata cggatgaaca ataa                                           24

<210> SEQ ID NO 96
<211> LENGTH: 19
<212> TYPE: DNA
<213> ORGANISM: Homo sapiens

<400> SEQUENCE: 96
gaagagtcgt ccctgctat                                                 19

<210> SEQ ID NO 97
<211> LENGTH: 21
<212> TYPE: DNA
<213> ORGANISM: Homo sapiens

<400> SEQUENCE: 97
tatgtagctt cctcctgaga a                                              21
```

<210> SEQ ID NO 98
<211> LENGTH: 25
<212> TYPE: DNA
<213> ORGANISM: Homo sapiens

<400> SEQUENCE: 98
agagaaagtt tttctggaat gtgtc                                          25

<210> SEQ ID NO 99
<211> LENGTH: 20
<212> TYPE: DNA
<213> ORGANISM: Homo sapiens

<400> SEQUENCE: 99
acagtgagcc tggtcccatt                                                20

<210> SEQ ID NO 100
<211> LENGTH: 19
<212> TYPE: DNA
<213> ORGANISM: Homo sapiens

<400> SEQUENCE: 100
accccgatgc cgactagat                                                 19

<210> SEQ ID NO 101
<211> LENGTH: 20
<212> TYPE: DNA
<213> ORGANISM: Homo sapiens

<400> SEQUENCE: 101
aggggtgaat tcgtatccaa                                                20

<210> SEQ ID NO 102
<211> LENGTH: 40
<212> TYPE: DNA
<213> ORGANISM: Homo sapiens
<220> FEATURE:
<221> NAME/KEY: MISC_FEATURE
<223> OTHER INFORMATION: additional exon in MAGE C2M

<400> SEQUENCE: 102
tcccagcaga caaactccct aggaagacag gagacctgtg                          40

<210> SEQ ID NO 103
<211> LENGTH: 35
<212> TYPE: DNA
<213> ORGANISM: Homo sapiens
<220> FEATURE:
<221> NAME/KEY: MISC_FEATURE
<223> OTHER INFORMATION: Exon sequence in MAGE C2M

<400> SEQUENCE: 103
aggccctaga gcaccacctt aagagaagaa gagct                               35

<210> SEQ ID NO 104
<211> LENGTH: 1983
<212> TYPE: DNA
<213> ORGANISM: Homo sapiens
<220> FEATURE:
<221> NAME/KEY: MISC_FEATURE
<223> OTHER INFORMATION: MAGE-C2 cDNA sequence

<400> SEQUENCE: 104
tgggaatctg acggatcgga ggcatttgtg aggaggcgcg aatcaagtta gcgggggaa     60

```
gagtcttaga cctggccagt cctcagggtg agggccctga ggaagaactg agggacctcc      120
caccatagag agaagaaacc ccggcctgta ctgcgctgcc gtgagactgg tgctccagga      180
accaggtggt gacgaactgg gtgtgaggca cacagcctaa agtcagcaca gcagaggagg      240
cccaggcagt gccaggagtc aaggcctgtt ggatctcatc atccatatcc ctgttgatac      300
gtttacctgc tgctcctgaa gaagtcgtca tgcctcccgt tccaggcgtt ccattccgca      360
acgttgacaa cgactccccg acctcagttg agttagaaga ctgggtagat gcacagcatc      420
ccacagatga ggaagaggag gaagcctcct ccgcctcttc cactttgtac ttagtatttt      480
cccctcttc tttctccaca tcctcttctc tgattcttgg tggtcctgag gaggaggagg      540
tgccctctgg tgtgatacca aatcttaccg agagcattcc cagtagtcct ccacagggtc      600
ctccacaggg tccttcccag agtcctctga gctcctgctg ctcctctttt tcatggagct      660
cattcagtga ggagtccagc agccagaaag gggaggatac aggcacctgt cagggcctgc      720
cagacagtga gtcctctttc acatatacac tagatgaaaa ggtggccgag ttagtggagt      780
tcctgctcct caaatacgaa gcagaggagc ctgtaacaga ggcagagatg ctgatgattg      840
tcatcaagta caaagattac tttcctgtga tactcaagag agcccgtgag ttcatggagc      900
ttcttttgg ccttgccctg atagaagtgg ccctgaccac ttctgtgtg tttgcaaaca      960
cagtaggcct caccgatgag ggtagtgatg atgagggcat gcccgagaac agcctcctga     1020
ttattattct gagtgtgatc ttcataaagg gcaactgtgc ctctgaggag gtcatctggg     1080
aagtgctgaa tgcagtaggg gtatatgctg ggagggagca cttcgtctat ggggagccta     1140
gggagctcct cactaaagtt tgggtgcagg acattaccct ggagtatcgg gaggtgcccc     1200
acagttctcc tccatattat gaattcctgt ggggtccaag agcccattca gaaagcatca     1260
agaagaaagt actagagttt ttagccaagc tgaacaacac tgttcctagt cctttccat      1320
cctggtacaa ggatgctttg aaagatgtgg aagagagagt ccaggccaca attgataccg     1380
cagatgatgc cactgtcatg gccagtgaaa gcctcagtgt catgtccagc aacgtctcct     1440
ttctgagtg aagtctagga tagtttcttc cccttgtgtt tgaacagggc agtttaggtt      1500
ctaggtagtg gagggccagg tggggctcga ggaacgtagt gttctttgca tttctgtccc     1560
atatgggtga tgtagagatt tacctgtttt tcagtatttt ctaaatgctt ttcctttgaa     1620
tagcaggtag ttagcttcag agtgttaatt tatgaatatt agtcgcacat gtattgctct     1680
ttatctggtt taagagtaac agtttgatat tttgttaaaa aaatggaaat accttctccc     1740
ttattttgtg atctgtaaca gggtagtgtg gtattgtaat aggcattttt tttttttttt     1800
acaatgtgca ataactcagc agttaaatag tggaacaaaa ttgaagggtg gtcagtagtt     1860
tcatttcctt gtcctgctta ttcttttgtt cttgaaaatt atatatacct ggctttgctt     1920
agcttgttga agaaagtagc agaaattaaa tcttaataaa agaaaaaaaa aaaaaaaaa      1980
agg                                                                  1983
```

<210> SEQ ID NO 105
<211> LENGTH: 373
<212> TYPE: PRT
<213> ORGANISM: Homo sapiens
<220> FEATURE:
<221> NAME/KEY: MISC_FEATURE
<223> OTHER INFORMATION: MAGE-C2

<400> SEQUENCE: 105

Met Pro Pro Val Pro Gly Val Pro Phe Arg Asn Val Asp Asn Asp Ser

```
            1               5                  10                 15
Pro Thr Ser Val Glu Leu Glu Asp Trp Val Asp Ala Gln His Pro Thr
                 20                  25                  30

Asp Glu Glu Glu Glu Ala Ser Ser Ala Ser Ser Thr Leu Tyr Leu
             35                  40                  45

Val Phe Ser Pro Ser Ser Phe Ser Thr Ser Ser Leu Ile Leu Gly
         50                  55                  60

Gly Pro Glu Glu Glu Val Pro Ser Gly Val Ile Pro Asn Leu Thr
65                  70                  75                  80

Glu Ser Ile Pro Ser Pro Pro Gln Gly Pro Gln Gly Pro Ser
                 85                  90                  95

Gln Ser Pro Leu Ser Ser Cys Cys Ser Ser Phe Ser Trp Ser Ser Phe
                 100                 105                 110

Ser Glu Glu Ser Ser Ser Gln Lys Gly Glu Asp Thr Gly Thr Cys Gln
                 115                 120                 125

Gly Leu Pro Asp Ser Glu Ser Ser Phe Thr Tyr Thr Leu Asp Glu Lys
             130                 135                 140

Val Ala Glu Leu Val Glu Phe Leu Leu Leu Lys Tyr Glu Ala Glu Glu
145                 150                 155                 160

Pro Val Thr Glu Ala Glu Met Leu Met Ile Val Ile Lys Tyr Lys Asp
                 165                 170                 175

Tyr Phe Pro Val Ile Leu Lys Arg Ala Arg Glu Phe Met Glu Leu Leu
                 180                 185                 190

Phe Gly Leu Ala Leu Ile Glu Val Gly Pro Asp His Phe Cys Val Phe
             195                 200                 205

Ala Asn Thr Val Gly Leu Thr Asp Glu Gly Ser Asp Asp Glu Gly Met
210                 215                 220

Pro Glu Asn Ser Leu Leu Ile Ile Leu Ser Val Ile Phe Ile Lys
225                 230                 235                 240

Gly Asn Cys Ala Ser Glu Glu Val Ile Trp Glu Val Leu Asn Ala Val
                 245                 250                 255

Gly Val Tyr Ala Gly Arg Glu His Phe Val Tyr Gly Glu Pro Arg Glu
                 260                 265                 270

Leu Leu Thr Lys Val Trp Val Gln Gly His Tyr Leu Glu Tyr Arg Glu
             275                 280                 285

Val Pro His Ser Ser Pro Pro Tyr Tyr Glu Phe Leu Trp Gly Pro Arg
             290                 295                 300

Ala His Ser Glu Ser Ile Lys Lys Lys Val Leu Glu Phe Leu Ala Lys
305                 310                 315                 320

Leu Asn Asn Thr Val Pro Ser Ser Phe Pro Ser Trp Tyr Lys Asp Ala
                 325                 330                 335

Leu Lys Asp Val Glu Glu Arg Val Gln Ala Thr Ile Asp Thr Ala Asp
             340                 345                 350

Asp Ala Thr Val Met Ala Ser Glu Ser Leu Ser Val Met Ser Ser Asn
             355                 360                 365

Val Ser Phe Ser Glu
    370

<210> SEQ ID NO 106
<211> LENGTH: 11
<212> TYPE: PRT
<213> ORGANISM: Homo sapiens

<400> SEQUENCE: 106
```

```
Ser Glu Ser Ile Lys Lys Lys Val Leu Glu Phe
1               5                   10

<210> SEQ ID NO 107
<211> LENGTH: 9
<212> TYPE: PRT
<213> ORGANISM: Homo sapiens

<400> SEQUENCE: 107

Ser Glu Ser Ile Lys Lys Lys Val Leu
1               5

<210> SEQ ID NO 108
<211> LENGTH: 10
<212> TYPE: PRT
<213> ORGANISM: Homo sapiens

<400> SEQUENCE: 108

Glu Ser Ile Lys Lys Lys Val Leu Glu Phe
1               5                   10

<210> SEQ ID NO 109
<211> LENGTH: 8
<212> TYPE: PRT
<213> ORGANISM: Homo sapiens

<400> SEQUENCE: 109

Glu Ser Ile Lys Lys Lys Val Leu
1               5

<210> SEQ ID NO 110
<211> LENGTH: 8
<212> TYPE: PRT
<213> ORGANISM: Homo sapiens

<400> SEQUENCE: 110

Ser Glu Ser Ile Lys Lys Lys Val
1               5

<210> SEQ ID NO 111
<211> LENGTH: 9
<212> TYPE: PRT
<213> ORGANISM: Homo sapiens

<400> SEQUENCE: 111

Ser Glu Val Ile Lys Arg Lys Val Val
1               5
```

MAGE-C2 ANTIGENIC PEPTIDES AND USES THEREOF

RELATED APPLICATIONS

This application is a divisional of application Ser. No. 11/044,051 filed Jan. 28, 2005, now patented, U.S. Pat. No. 7,348,007, which claims priority to U.S. provisional patent application No. 60/542,540, entitled Mage-C2 Antigenic Peptides and Uses Thereof, filed Feb. 9, 2004.

FIELD OF THE INVENTION

This invention relates to isolated peptides which bind to HLA, particularly HLA-A2, HLA-B57, or HLA-B44 and uses thereof. The peptides are derived from members of the MAGE family of tumor rejection antigen precursors. This invention also relates to nucleic acid molecules encoding the peptides, complexes of the peptides and HLA molecule, and to cells expressing the HLA/peptide complexes on their surfaces, as well as uses of the nucleic acid molecules, the HLA/peptide complexes, and the cells expressing the complexes in the diagnosis and treatment of pathological conditions.

BACKGROUND

The process by which the mammalian immune system recognizes and reacts to foreign or alien materials is a complex one. An important facet of the system is the T cell response. This response requires that T cells recognize and interact with complexes of cell surface molecules, referred to as human leukocyte antigens ("HLAs"), or major histocompatibility complexes ("MHCs"), and peptides. The peptides are derived from larger molecules which are processed by the cells which also present the HLA/MHC molecule. See in this regard Male et al., *Advanced Immunology* (J.P. Lipincott Company, 1987), especially chapters 6-10. The interaction of T cell and complexes of HLA/peptide is restricted, requiring a T cell specific for a particular combination of an HLA molecule and a peptide. If a specific T cell is not present, there is no T cell response even if its partner complex is present. Similarly, there is no response if the specific complex is absent, but the T cell is present. This mechanism is involved in the immune system's response to foreign materials, in autoimmune pathologies, and in responses to cellular abnormalities. Much early work focused on the mechanisms by which proteins are processed into the HLA binding peptides. See, in this regard, Barinaga, *Science* 257: 880 (1992); Fremont et al., *Science* 257: 919 (1992); Matsumura et al., *Science* 257: 927 (1992); Latron et al., *Science* 257: 964 (1992).

The mechanism by which T cells recognize cellular abnormalities has also been implicated in cancer. For example, PCT application PCT/US92/04354, filed May 22, 1992, published on Nov. 26, 1992, and incorporated by reference, discloses a family of genes that are processed into peptides which, in turn, are expressed on cell surfaces and lead to lysis of the tumor cells by specific CTLs. The genes are said to code for "tumor rejection antigen precursors" or "TRAP" molecules, and the peptides derived therefrom are referred to as "tumor rejection antigens" or "TRAs". See Traversari et al., *Immunogenetics* 35: 145 (1992); van der Bruggen et al., *Science* 254: 1643 (1991) and U.S. Pat. No. 5,342,774 and U.S. Pat. No. 5,462,871.

Other families of genes encoding TRAPs are also known in the art, see e.g., U.S. Pat. No. 5,629,166 for information relating to MAGE-1 TRAP and TRAs; Lucas et al., *Cancer Res.*, 58(4):743-52 (1998), Chen et al., *PNAS,* 95(12):6919-23 (1998), Jungbluth et al., *Int. J. Canc.* 94(2):252-6 (2001), Jungbluth et al., *Int J. Canc.* 99(6):839-45 (2002), Chomez et al., An overview of the MAGE gene family with the identification of all human members of the family. *Cancer Res.* 2001 Jul. 15; 61(14):5544-51, Rimoldi et al., cDNA and protein characterization of human MAGE-10. *Int J Cancer*. September 9; 82(6):901-7 (1999), Lurquin et al., Two members of the human MAGE-B gene family located in Xp21.3 are expressed in tumors of various histological origins. *Genomics*. December 15; 46(3):397-408 (1997), De Plaen et al., Structure, chromosomal localization, and expression of 12 genes of the MAGE family. *Immunogenetics*. 40:360-269 (1994), U.S. Pat. No. 5,997,872 issued Dec. 7, 1999, PCT/US98/08493 filed Apr. 24, 1998 and U.S. patent application Ser. No. 09/501,104 filed Feb. 9, 2000 for information relating to MAGE-C1, MAGE C2, MAGE-C3, MAGE-B1, MAGE B2, MAGE-B3, MAGE-B5, MAGE-B6, MAGE-A10 and MAGE A11 TRAPs and TRAs; U.S. Pat. No. 5,571,711 issued Jan. 5, 1996 for information relating to BAGE TRAPs and TRAs; U.S. Pat. No. 5,571,711 issued Jan. 5, 1996 for information relating to tyrosinase TRAP and TRAs; U.S. patent application Ser. No. 08/096,039 and Ser. No. 08/250,162, for information relating to GAGE TRAP and TRA, and; U.S. application Ser. No. 08/316,231 filed Sep. 30, 1994, (DAGE TRAPs), all the foregoing applications and patents are incorporated by reference in their entirety.

U.S. Pat. No. 5,405,940, incorporated by reference, describes the MAGE-1 gene coding for a tumor rejection antigen precursor that is processed to nonapeptides, which are presented by the HLA-A1 molecule. The nonapeptides which bind to HLA-A1 follow a "rule" for binding in that a motif is satisfied. In this regard, see, e.g., PCT/US93/07421; Falk et al., *Nature* 351:290-296 (1991); Engelhard, *Ann Rev. Immunol.* 12:181-207 (1994); Ruppert et al., *Cell* 74:929-937 (1993); Rötzschke et al., *Nature* 348:252-254 (1990); Bjorkman et al., *Nature* 329:512-518 (1987); Traversari et al., *J. Exp. Med.* 176:1453-1457 (1992). Because different individuals possess different HLA phenotypes, identification of a particular peptide as being a partner for a particular HLA molecule has diagnostic and therapeutic ramifications, only for individuals with that particular HLA phenotype. Thus, there is a need for further work in the area, because cellular abnormalities are not restricted to one particular HLA phenotype, and targeted therapy requires some knowledge of the phenotype of the abnormal cells at issue.

After 48 hours, the production of TNF by the TIL was measured by assaying the toxicity of the supernatant on TNF-sensitive WEHI-164.13 cells. Values represent means of triplicate cultures.

Figure 3:
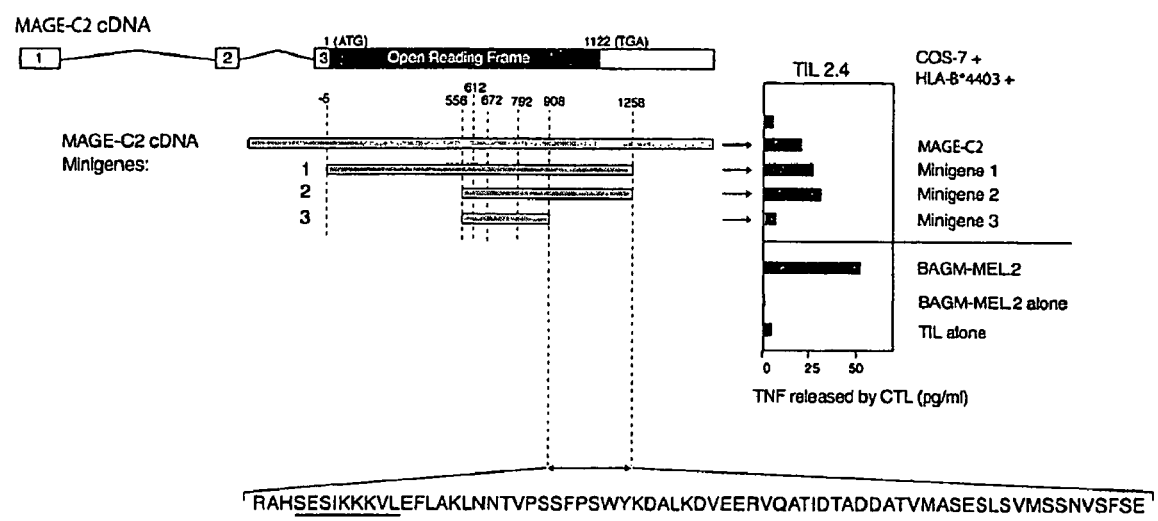

FIG. 3 depicts the localization of the antigenic peptide recognized by the TIL 2.4 clone. The TIL were incubated with COS-7 cells that were cotransfected with HLA-B44 and the cDNA of MAGE-C2 or the various minigenes recited in the left of the figure. After incubating the TIL and transfected COS-7 cells for 24 hours, the level of TNF released by the TIL was measured by assaying the toxicity of the culture supernatant on TNF-sensitive WEHI-164.13. cells. The sequence of the recognized antigenic peptide (SEQ ID NO: 107) binding to HLA-B44 is underlined (see FIG. 4).

Figure 4:
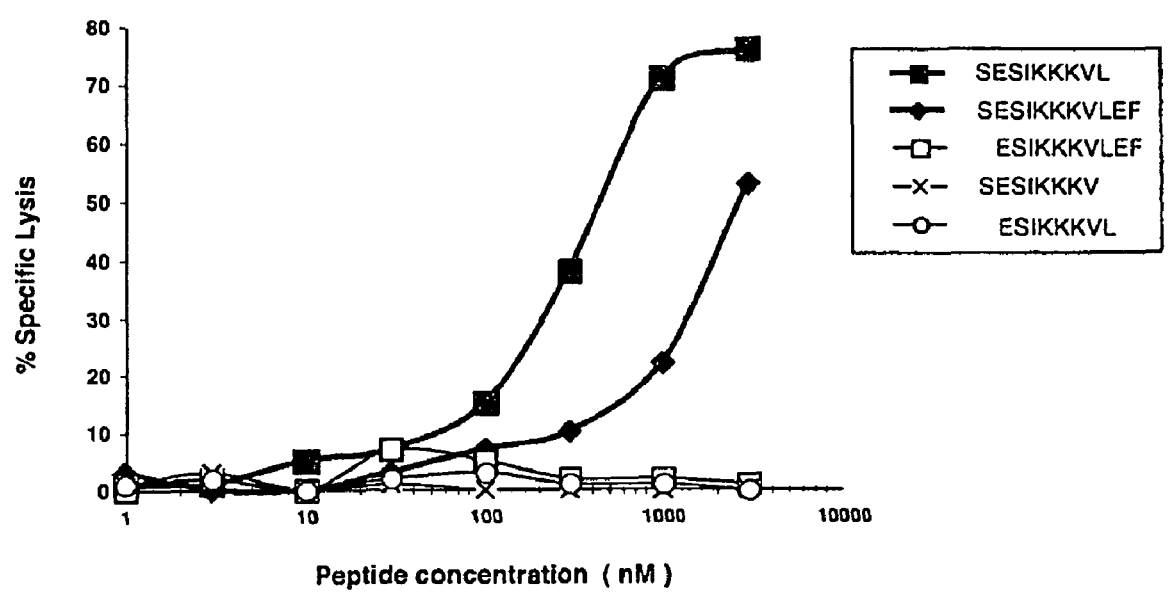

FIG. 4 depicts the lysis of BAGM-EBV cells pulsed with the MAGE.C2.B44 peptides. The $Cr^{51}$ labeled BAGM-EBV cells were incubated with various concentrations of the 11-mer MAGE-C2 peptide SESIKKKVLEF (SE ID NO: 106) binding to HLA-B44 (-•-) and truncated peptides, SESIKKKVL (SEQ ID NO: 107), ESIKKKVLEF (SEQ ID NO: 108), SESIKKKV (SEQ ID NO: 110) and ESIKKKVL (SEQ ID NO: 109). TIL2.4 was added at a ratio of 15:1. The chromium release was measured after 4 hours. The nonapeptide (-■-) is the antigenic sequence recognized by the TIL.

SUMMARY OF THE INVENTION

Disclosed herein is the identification of peptides derived from MAGE-C2 that bind to HLA molecules, particularly HLA-A2, HLA-B57 or HLA-B44 molecules. Also disclosed are nucleic acid molecules that encode the peptides, complexes of the peptides and HLA molecules and methods for using the peptides and complexes comprising the peptides in diagnostic and therapeutic assays.

This invention relates to isolated peptides consisting of the amino acid sequence ALKDVEERX (SEQ ID NO: 1) or LKDVEERV (SEQ ID NO: 2), particularly an isolated peptide consisting of the amino acid sequence ALKDVEERX wherein X may be any amino acid, preferably a hydrophobic amino acid, more preferably X is Ala, Val, Leu, Ile, Pro, Phe, Met, Trp or Glu and most preferably X is an valine (SEQ ID NO: 3) or alanine (SEQ ID NO: 5).

This invention also relates to the isolated peptides recited in Table 2, infra.

This invention also relates to isolated peptides consisting of the amino acid sequence XLFGLALIEV (SEQ ID NO: 88) wherein X may be absent or may be any amino acid, preferably a hydrophobic amino acid, more preferably X is Ala, Val, Leu, Ile, Pro, Phe, Met, Trp or Glu and most preferably X is a leucine (SEQ ID NO: 77).

This invention also relates to isolated peptides consisting of the amino acid sequence ASSTLYLVF (SEQ ID NO: 89), SESIKKKVLEF (SEQ ID NO: 106), SESIKKKVL (SEQ ID NO: 107), or SEVIKRKVV, SEQ ID NO: 111.

This invention relates to a composition useful in provoking a cytolytic T cell response comprising the isolated peptide consisting of the amino acid sequences ALKDVEERX (SEQ ID NO: 1), wherein X is any amino acid, preferably X is a hydrophobic amino acid, more preferably X is Ala, Val, Leu, Ile, Pro, Phe, Met, Trp or Glu and most preferably X is an alanine (SEQ ID NO: 5) or a valine (SEQ ID NO: 3) or the isolated peptide consists of the amino acid sequence LKDVEERV (SEQ ID NO: 2), particularly the composition comprises an isolated peptide consisting of the amino acid sequence ALKDVEERV (SEQ ID NO: 3) and an adjuvant. The composition may comprise at least one additional peptide.

This invention also relates to compositions useful for provoking a CTL response comprising an adjuvant and an isolated peptide of Table 2, infra. The composition may comprise an additional peptide.

This invention also relates to compositions useful for provoking a CTL response comprising an adjuvant and an isolated peptide consisting of the amino acid sequence of XLFGLALIEV (SEQ ID NO: 88) wherein X may be absent or may be any amino acid, preferably a hydrophobic amino acid, more preferably X is Ala, Val, Leu, Ile, Pro, Phe, Met, Trp or Glu and most preferably X is a leucine (SEQ ID NO: 77). The composition may comprise at least one additional peptide.

This invention relates to compositions useful for provoking a CTL response comprising an adjuvant and an isolated peptide consisting of the amino acid sequence of ASSTLYLVF (SEQ ID NO: 89). The composition may comprise at least one additional peptide.

This invention relates to compositions useful for provoking a CTL response comprising an adjuvant and an isolated peptide consisting of the amino acid sequence of SESIKKKVL SEQ ID NO: 107 or SEVIKRKVV SEQ ID NO: 111. The composition may comprise at least one additional peptide.

This invention also relates to an isolated nucleic acid molecule comprising a nucleotide sequence which encodes the peptide of SEQ ID NO: 1, 2, 88, 78, 89, 106, 107 or 111, or the peptides recited in Table 2, infra, preferably SEQ ID NO: 1, 2, 88, 78, 89, 106, 107 or 111 with the proviso that the isolated nucleic acid molecule which encodes the peptide does not encode MAGE-C1 (SEQ ID NO: 73) or MAGE-C2 (SEQ ID NO: 71). The isolated nucleic acid molecule may consist of a nucleotide sequence that encodes a peptide consisting of the amino acid sequence ALKDVEERX (SEQ ID NO: 1) wherein X may be any amino acid, preferably any hydrophobic amino acid, more preferably X is Ala, Val, Leu, Ile, Pro, Phe, Met, Trp or Glu and most preferably X is an valine (SEQ ID NO: 3) or alanine (SEQ ID NO: 5), or the nucleic acid molecule may consist of a nucleotide sequence that encodes a peptide consisting of the amino acid sequence LKDVEERV (SEQ ID NO: 2). The isolated nucleic acid molecule may consist of a nucleotide sequence that encodes a peptide consisting of the amino acid sequence XLFGLALIEV (SEQ ID NO: 88) wherein X is absent or any other amino acid particularly leucine (SEQ ID NO: 77), or the isolated nucleic acid molecule may consist of a nucleotide sequence that encodes a peptide consisting of the amino acid sequence ASSTLYLVF (SEQ ID NO: 89). The isolated nucleic acid molecule may consist of a nucleotide sequence that encodes a peptide consisting of an amino acid sequence recited in Table 2, infra. The isolated nucleic acid molecule may consist of a nucleotide sequence that encodes a peptide consisting of an amino acid sequence SESIKKKVL SEQ ID NO: 107 or SEVIKRKVV SEQ ID NO: 111.

Those of skill in the art appreciate that there is degeneracy in the genetic code and thus more than one codon my encode a single amino acid. Those of skill in the art also appreciate that once provided with the amino acid sequence of a peptide it would take routine effort using standard techniques to generate all the nucleotide sequences that would encode a particular peptide and generate nucleic acid molecules that encode the particular peptide without listing all those sequences herein. Such nucleic acid molecules, which encode the particular peptides of this invention, are also a part of this invention.

Also an aspect of this invention is an expression vector comprising a plurality of nucleotide sequences which encode peptides which bind to MHC molecules, wherein at least one of said peptides is the peptide consisting of the amino acid sequences ALKDVEERX (SEQ ID NO: 1), wherein the X may be any amino acid preferably any hydrophobic amino acid, more preferably X is Ala, Val, Leu, Ile, Pro, Phe, Met, Trp or Glu and most preferably X is valine, ALKDVEERV (SEQ ID NO: 3), or alanine (SEQ ID NO: 5) or at least one of the peptides consists of the amino acid sequence set forth in SEQ ID NO: 2 (LKDVEERV). At least one of the nucleotide sequences which encodes a peptide which binds to MHC molecules may also be a nucleotide sequence that encodes XLFGLALIEV (SEQ ID NO: 88), wherein X may be absent or any amino acid, preferably X is leucine (SEQ ID NO: 77) or LFGLALIEV (SEQ ID NO: 78). The nucleotide sequence which encodes a peptide which binds to the MHC molecules may be a nucleotide sequence that encodes ASSTLYLVF (SEQ ID NO: 89).

Also an aspect of this invention is an expression vector comprising a plurality of nucleotide sequences which encode peptides which bind to MHC molecules, wherein at least one of said peptides is the peptide consisting of the amino acid sequences SESIKKKVLEF (SEQ ID NO: 106), SESIKKKVL (SEQ ID NO: 107) or SEVIKRKVV SEQ ID NO: 111.

This invention relates to a recombinant cell transformed or transfected with an isolated nucleic acid molecule comprising a nucleotide sequence which encodes a peptide comprising the amino acid sequence ALKDVEERX (SEQ ID NO: 1), wherein X may be any amino acid, preferably any hydrophobic amino acid and more preferably X is an alanine (SEQ ID NO: 5) or a valine (SEQ ID NO: 3), particularly the isolated nucleic acid molecule encodes a peptide comprising the amino acid sequence ALKDVEERV (SEQ ID NO: 3), or the peptide comprises the sequence LKDVEERV (SEQ ID NO: 2), with the proviso that the isolated nucleic acid molecule does not encode MAGE-C1 (SEQ ID NO: 73) or MAGE-C2 (SEQ ID NO: 71). The recombinant host cell may also be transformed or transfected with a nucleic acid molecule that encodes an HLA molecule, particularly an HLA-A2 molecule.

The invention relates to a recombinant cell transformed or transfected with an isolated nucleic acid molecule comprising a nucleotide sequence which encodes a peptide comprising an amino acid sequence recited in Table 2, infra. The recombinant host cell may be transformed or transfected with a nucleic acid molecule that encodes an HLA molecule, particularly HLA-A2.

This invention relates to a recombinant cell transformed or transfected with an isolated nucleic acid molecule comprising a nucleotide sequence which encodes a peptide comprising the amino acid sequence XLFGLALIEV (SEQ ID NO: 88), wherein X may be absent or may be any amino acid, preferably X is leucine, or LFGLALIEV (SEQ ID NO: 78), with the proviso that the isolated nucleic acid molecule does not encode MAGE-C1 (SEQ ID NO: 73) or MAGE-C2 (SEQ ID NO: 71). The isolated nucleic acid molecule may consist of a nucleotide sequence that consists of the amino acid sequence XLFGLALIEV (SEQ ID NO: 88), wherein X may be absent or may be any amino acid, preferably X is leucine, or LFGLALIEV (SEQ ID NO: 78), with the proviso that the isolated nucleic acid molecule does not encode MAGE-C1 (SEQ ID NO: 73) or MAGE-C2 (SEQ ID NO: 71). The recombinant host cell may also be transformed or transfected with a nucleic acid molecule that encodes an HLA molecule, particularly an HLA-A2 molecule.

This invention also relates to a recombinant cell transformed or transfected with an isolated nucleic acid molecule comprising a nucleotide sequence which encodes a peptide comprising the amino acid sequence ASSTLYLVF (SEQ ID NO: 89) with the proviso that the isolated nucleic acid molecule does not encode MAGE-C1 (SEQ ID NO: 73) or MAGE-C2 (SEQ ID NO: 71) or the nucleic acid molecule may consist of a sequence that encodes a peptide consisting of the amino acid sequence ASSTLYLVF (SEQ ID NO: 89). The recombinant host cell may also be transformed or transfected with a nucleic acid molecule that encodes an HLA molecule, particularly an HLA-B57 molecule.

This invention also relates to a recombinant cell transformed or transfected with an isolated nucleic acid molecule comprising a nucleotide sequence which encodes a peptide comprising the amino acid sequence SESIKKKVLEF (SEQ ID NO: 106), SESIKKKVL (SEQ ID NO: 107) or SEVIKRKVV SEQ ID NO: 111 with the proviso that the isolated nucleic acid molecule does not encode MAGE-C1 (SEQ ID NO: 73) or MAGE-C2 (SEQ ID NO: 71) or the nucleic acid molecule may consist of a sequence that encodes a peptide consisting of the amino acid sequence SESIKKKVLEF (SEQ ID NO: 106), SESIKKKVL (SEQ ID NO: 107) or SEVIKRKVV SEQ ID NO: 111. The recombinant host cell may also be transformed or transfected with a nucleic acid molecule that encodes an HLA molecule, particularly an HLA-B44 molecule.

A further aspect of this invention is a recombinant cell transformed or transfected with an expression vector comprising a nucleic acid molecule that encodes one or more peptides that bind to HLA molecules in operable linkage with a promoter, wherein at least one of said peptides consists of the amino acid sequence XLFGLALIEV (SEQ ID NO: 88), wherein X is absent or any other amino acid, particularly leu (SEQ ID NO: 77), or ALKDVEERX (SEQ ID NO: 1) or LKDVEERV (SEQ ID NO: 2). The final amino acid X in SEQ ID NO: 1 may be any amino acid, preferably X is any hydrophobic amino acid, and more preferably X is alanine (SEQ ID NO: 5) or valine, e.g., ALKDVEERV (SEQ ID NO: 3). The recombinant host cell may also be transformed or transfected with a nucleic acid molecule that encodes an HLA molecule, particularly an HLA-A2 molecule, in operable linkage with a promoter. The nucleic acid molecules that encode the peptide and the HLA molecule may be within a single vector or may be on separate vectors.

This invention relates to a recombinant cell transformed or transfected with an expression vector comprising a nucleic acid molecule that encodes one or more peptides that bind to HLA molecules inoperable linkage with a promoter, wherein at least one of said peptide consists of amino acid sequence recited in Table 2, infra. The recombinant host cell may be transformed or transfected with a nucleic acid molecule that encodes an HLA molecule, particularly an HLA-A2. The nucleic acid molecules that encode the HLA and peptide may be within a single vector or separate vectors.

Another aspect of this invention is a recombinant cell transformed or transfected with an expression vector comprising a nucleic acid molecule that encodes one or more peptides that bind to HLA molecules in operable linkage with a promoter, wherein at least one of said peptides consists of the amino acid sequence ASSTLYLVF (SEQ ID NO: 89) with the proviso that the isolated nucleic acid molecule does not encode MAGE-C1 (SEQ ID NO: 73) or MAGE-C2 (SEQ ID NO: 71). The recombinant host cell may also be transformed or transfected with a nucleic acid molecule that encodes an HLA molecule, particularly an HLA-B57 molecule, in operable linkage with a promoter. The nucleic acid molecules that encode the peptide and the HLA molecule may be within a single vector or may be on separate vectors.

Another aspect of this invention is a recombinant cell transformed or transfected with an expression vector comprising a nucleic acid molecule that encodes one or more peptides that bind to HLA molecules in operable linkage with a promoter, wherein at least one of said peptides consists of the amino acid sequence SESIKKKVLEF (SEQ ID NO: 106), SESIKKKVL (SEQ ID NO: 107) or SEVIKRKVV (SEQ ID NO: 111) with the proviso that the isolated nucleic acid molecule does not encode MAGE-C1 (SEQ ID NO: 73) or MAGE-C2 (SEQ ID NO: 71). The recombinant host cell may also be transformed or transfected with a nucleic acid molecule that encodes an HLA molecule, particularly an HLA-B44 molecule, in operable linkage with a promoter. The nucleic acid molecules that encode the peptide and the HLA molecule may be within a single vector or may be on separate vectors.

Also an aspect of this invention are methods for determining if a cell presents an HLA molecule, particularly an HLA-A2 molecule, on its surface comprising contacting a sample containing said cell with a peptide consisting of the amino acid sequence ALKDVEERX (SEQ ID NO: 1), wherein X may be any amino acid, preferably any hydrophobic amino acid and more preferably alanine (SEQ ID NO: 5) or valine (SEQ ID NO: 3), or a peptide consisting of the amino acid sequence LKDVEERV (SEQ ID NO: 2), and determining binding therebetween, wherein said binding is indicative of the HLA molecule, e.g., HLA-A2 on the surface of said cell. Methods of this invention for determining if a cell presents a particular HLA molecule, e.g. an HLA-A2 molecule, on its surface also comprise contacting a sample containing the cell to be tested with a peptide consisting of the amino acid sequence XLFGLALIEV (SEQ ID NO: 88), wherein X may be absent or any amino acid, particularly leucine (SEQ ID NO: 77). The binding of the peptide to the HLA molecule, e.g., HLA-A2, may be determined by contacting the cells with a CTL which recognizes a complex of the peptide and the HLA, e.g., HLA-A2, and assaying for cell lysis by the CTLs, proliferation of the CTLs or release of TNF-α by the CTLs by using standard assays.

Also an aspect of this invention are methods for determining if a cell presents an HLA molecule, particularly an HLA-B57 molecule, on its surface comprising contacting a sample containing said cell with a peptide consisting of the amino acid sequence ASSTLYLVF (SEQ ID NO: 89). The binding of the peptide to the HLA molecule may be determined by contacting the cells with a CTL which recognizes a complex of the peptide and the HLA, e.g., HLA-B57, and assaying for cell lysis by the CTLs, proliferation of the CTLs or release of TNF-α by the CTLs by using standard assays.

Also an aspect of this invention are methods for determining if a cell presents an HLA molecule, particularly an HLA-B44 molecule, on its surface comprising contacting a sample containing said cell with a peptide consisting of the amino acid sequence SESIKKKVLEF (SEQ ID NO: 106), SESIKKKVL (SEQ ID NO: 107) or SEVIKRKVV (SEQ ID NO: 111). The binding of the peptide to the HLA molecule may be determined by contacting the cells with a CTL which recognizes a complex of the peptide and the HLA, e.g., HLA-B44, and assaying for cell lysis by the CTLs, proliferation of the CTLs or release of TNF-α by the CTLs by using standard assays.

This invention also relates to an isolated polytope molecule, wherein at least a portion of which comprises the amino acid sequence consisting of ALKDVEERX (SEQ ID NO: 1) wherein X may be any amino acid, preferably any hydrophobic amino acid and more preferably X is alanine (SEQ ID NO: 5) or valine (SEQ ID NO: 3), or the amino acid sequence consisting of LKDVEERV (SEQ ID NO: 2), or, a portion of the polytope may comprise the amino acid sequence consisting of XLFGLALIEV (SEQ ID NO: 88), wherein the X is absent or any amino acid particularly leucine (SEQ ID NO: 77) or a portion of the polytope may comprise the amino acid sequence consisting of ASSTLYLVF (SEQ ID NO: 89). The invention also relates to polytopes, wherein at least a portion of which comprises an amino acid sequence recited in Table 2, infra. The invention also relates to polytopes, wherein at least a portion of which comprises an amino acid sequence SESIKKKVV SEQ ID NO: 107 or SEVIKRKVV SEQ ID NO: 111.

Also a part of this invention is a nucleic acid molecule that encodes the polytopes of this invention, expression vectors that comprise the nucleic acid molecules of this invention in operable linkage with a promoter and host cells transformed or transfected with the vectors.

This invention relates to methods for determining if a cytolytic T cell (CTL) specific for complexes of an HLA-A2 molecule and a peptide is present in a sample, comprising admixing said sample with an HLA-A2 molecule and a peptide consisting of ALKDVEERX (SEQ ID NO: 1), preferably X is any hydrophobic amino acid and more preferably X is a valine (SEQ ID NO: 3) or an alanine (SEQ ID NO: 5), or a peptide consisting of the sequence LKDVEERV (SEQ ID NO: 2), or a peptide consisting of the sequence XLFGLA-LIEV (SEQ ID NO: 88), wherein X may be absent or any amino acid, particularly leucine (SEQ ID NO: 77) and determining an interaction between the CTL and complexes of the HLA-A2 molecule and the peptide to determine the specificity of the CTL.

This invention relates to methods for determining if a cytolytic T cell (CTL) specific for complexes of an HLA-B57 molecule and a peptide is present in a sample, comprising admixing said sample with an HLA-B57 molecule and a peptide consisting of ASSTLYLVF (SEQ ID NO: 89) and determining an interaction between the CTL and complexes of the HLA-B57 molecule and the peptide to determine the specificity of the CTL.

This invention relates to methods for determining if a cytolytic T cell (CTL) specific for complexes of an HLA-B44 molecule and a peptide is present in a sample, comprising admixing said sample with an HLA-B44 molecule and a peptide consisting of SESIKKKVV SEQ ID NO: 107) or SEVIKRKVV SEQ ID NO: 111 and determining an interaction between the CTL and complexes of the HLA-B44 molecule and the peptide to determine the specificity of the CTL.

Another aspect of this invention is an isolated complex useful in isolating a cytolytic T cell. The isolated complex comprises a first and second binding partner which are specific to each other, wherein the second binding partner is bound to a plurality of "tetramers" of an HLA-A2 molecule, a $\beta_2$ microglobulin molecule, and a peptide consisting of ALKDVEERX (SEQ ID NO: 1) wherein X is any amino acid, preferably X is an alanine (SEQ ID NO: 5) or valine (SEQ ID NO: 3) or the peptide consists of LKDVEERV (SEQ ID NO: 2). Preferably the peptide consists of the amino acid sequence ALKDVEERX (SEQ ID NO: 1) and more preferably the peptide consists of the amino acid sequence ALKDVEERV (SEQ ID NO: 3). The peptide in the plurality of tetramers may also consist of the sequence XLFGLALIEV (SEQ ID NO: 88) wherein X is absent or is any other amino acid, particularly leucine (SEQ ID NO: 77). Preferably the first binding partner is avidin and the second binding partner is biotin.

Another aspect of this invention is an isolated complex useful in isolating a cytolytic T cell. The isolated complex comprises a first and second binding partner which are specific to each other, wherein the second binding partner is bound to a plurality of "tetramers" of an HLA-B57 molecule, a β₂ microglobulin molecule, and a peptide consisting of ASSTLYLVF (SEQ ID NO: 89). Preferably, the first binding partner is avidin and the second binding partner is biotin.

Another aspect of this invention is an isolated complex useful in isolating a cytolytic T cell. The isolated complex comprises a first and second binding partner which are specific to each other, wherein the second binding partner is bound to a plurality of "tetramers" of an HLA-B44 molecule, a β₂ microglobulin molecule, and a peptide consisting of SESIKKKVLEF (SEQ ID NO: 106), SESIKKKVL (SEQ ID NO: 107) or SEVIKRKVV (SEQ ID NO: 111). Preferably, the first binding partner is avidin and the second binding partner is biotin.

The construction of such tetramers is disclosed in U.S. patent application Ser. No. 09/275,993 filed Mar. 24, 1999 incorporated herein by reference, see also Dunbar et al., *Curr. Biol.* 8:4132-416 (1998) incorporated herein by reference. The first binding partner may be e.g., avidin or streptavidin and the second binding partner may be e.g., biotin. The HLA molecule and β₂ microglobulin refold into a complex which is then biotinylated with biotin holoenzyme synthase and then combined with labeled streptavidin or labeled avidin to produce tetrameric structures. The tetrameric structures are mixed with the particular peptides and the multicomponent complex ("tetramer") is then used to identify CTL cells that are specific for the complex of HLA and peptide. The tetramers in some circumstances may also stimulate the CTL cells to release cytokines or proliferate. The complex may further comprise a label. For example the first or second binding partner may be labeled with a radiolabel, a fluorescent label or a peptide tag such as a c-myc or His6 peptide. Methods for labeling peptides and proteins are known in the art. See e.g., Evan et al. *Mol. Cell. Biol.*, 5:3610-3616 (1985) and Mukhija, "High level production and one-step purification of biologically active human growth hormone in *Escherichia coli*", Gene 165:303-306 (1995); Goldenberg "Current status of cancer imaging with radiolabeled antibodies, *Cancer Res. Clin. Oncol.*, 113: 203-208 (1987); Carter and Merchant, "Engineering antibodies for imaging and therapy", *Curr. Opin. Biotechnol.*, 8:449-454 (1997), and; Bailey, "Labeling of peptides and proteins by radioiodination", *Method Mol. Biol.*, 32:441-448 (1994) (all incorporated herein by reference) for a general discussion of methods useful for labeling antibody molecules and other polypeptides for identification or isolation purposes.

Compositions comprising the tetramers are also part of this invention, as are methods for using the tetramers to identify CTLs which recognize specific HLA/peptide complexes and to methods of stimulating the CTLs with the tetramers. The composition may also comprise a carrier, and/or an adjuvant. The carrier and adjuvant may be any that are pharmaceutically acceptable and routinely used in the art. E.g. the carrier may be DMSO and the adjuvant may be GM-CSF or IL-12.

A further aspect of this invention are methods for identifying or isolating cytolytic T cells in a sample, comprising admixing the sample with the complex described above, and identifying or isolating CTLs which bind thereto. Methods for determining the presence of a CTL in a sample are well known in the art. For example, one may assay for proliferation of the CTL cells in response to exposure to the complex or one may assay the sample admixed with the complex for lysis of cells expressing a complex of the peptide and an HLA molecule or one may assay for the release of TNF by the CTLs. See e.g. Herin et al., *Int. J. Cancer* 39: 390-396 (1987); Been et al. *J. Exp. Med.* 152: 1184-1193 (1980) and; Traversari et al., *Immunogenetics* 35:145-152 (1992) all incorporated herein by reference.

Still another aspect of this invention is a method for monitoring status of a tumor presenting complexes of a peptide and an HLA molecule, particularly the peptides of this invention and HLA-A2, HLA-B57 or HLA-B44, comprising contacting a sample taken from a patient with a tumor with the isolated complexes described above and assaying the level of CTL response in the sample. That response is then compared to a control, e.g., the CTL response measured in a sample from a patient having tumors presenting the complexes and having a known status or a sample from a patient who has no detectable tumors. By monitoring the magnitude of the response by the CTLs in the sample from the test patient as compared to the controls one may monitor the status of the tumor in the test patient.

The peptides of this invention either alone or in complex with an HLA molecule, e.g. HLA-A2, HLA-B57 or HLA-B44, are useful for inducing an immune response in a subject in need thereof, e.g., the production of antibodies or the stimulation of CTLs, which result in tumor regression or in slowing the progression of the tumor wherein the tumors present complexes of peptide and HLA. Methods for inducing an immune response in a subject may comprise administering a composition comprising a peptide of this invention or complexes of the peptide and HLA molecules, e.g., cells presenting an HLA/peptide complex on their surfaces or tetramers as described above, to a subject wherein the amount of the composition administered is sufficient to induce an immune response, either humoral or cellular, which results in tumor regression or in slowing the progression of the tumor.

If cells expressing the peptide are administered to a subject they should be cells that do not have harmful effects on the subject, e.g., the cells may be irradiated such that they do not proliferate in the subject but still display the complex of HLA and peptide, and the cells should be non-tumorigenic. The cells may be autologous and may be transfected with a nucleic acid molecule that encodes the peptide or may be transfected with a nucleic acid molecule that encodes the HLA molecule, e.g., HLA-A2, HLA-B57 or HLA-B44. The cells may also be transfected with a nucleic acid molecule that encodes both the peptide and the HLA molecule.

An agent that provokes a response by a CTL specific for the peptide HLA complexes described herein, e.g., the peptides, polytope or tetramer complexes of the peptides and HLA molecules of this invention, compositions comprising the peptides, polytopes or complexes of this invention, or cells expressing the complex of HLA and peptide, e.g., cells transfected with nucleic acid molecules that encode the HLA and/or the peptide, preferably a MAGE-C2 or MAGE-C1 derived peptide, or the protein, preferably MAGE-C2 or MAGE-C1, that is processed into the peptides, may be used in treating a subject with a disorder. Preferably the disorder is characterized by the presence of complexes of an HLA molecule, particularly an HLA-A2, HLA-B57 or HLA-B44 molecule, and a peptide of this invention, particularly a peptide having an amino acid sequence selected from the group consisting of SEQ ID NO: 1, SEQ ID NO: 2, SEQ ID NO: 3, SEQ ID NO: 5, SEQ ID NO: 77, SEQ ID NO: 78, SEQ ID NO: 88, SEQ ID NO: 89, SEQ ID NO: 106, SEQ ID NO: 107 and SEQ ID NO: 111, presented on cell surfaces.

This invention relates to a method for treating a subject with a disorder characterized by the presence of complexes of an HLA molecule, particularly an HLA-A2, HLA-B57 or HLA-B44 molecule, and a peptide of this invention, particularly a peptide having an amino acid sequence selected from the group consisting of SEQ ID NO: 1, SEQ ID NO: 2, SEQ ID NO: 3, SEQ ID NO: 5, SEQ ID NO: 77, SEQ ID NO: 78, SEQ ID NO: 88, SEQ ID NO: 89, SEQ ID NO: 106, SEQ ID NO: 107 and SEQ ID NO: 111 presented on cell surfaces by administering the peptides of this invention to the subject in an amount that is sufficient to stimulate CTLs specific for complexes of an HLA and the peptide in sufficient numbers to alleviate the disorder. The peptide may be administered in conjunction with an adjuvant or may also be a part of a composition comprising one or more additional HLA-binding peptides. The generation and proliferation of the CTLs may be monitored by any means known in the art.

This invention further relates to a method for treating a subject with a disorder characterized by the presence of complexes of an HLA molecule, particularly HLA-A2, HLA-B57 or HLA-B44, and a peptide of this invention, particularly one selected from the group consisting of SEQ ID NO: 1, SEQ ID NO: 2, SEQ ID NO: 3, SEQ ID NO: 5, SEQ ID NO: 77, SEQ ID NO: 78, SEQ ID NO: 88, SEQ ID NO: 89, SEQ ID NO: 106, SEQ ID NO: 107 or SEQ ID NO: 111, on cell surfaces by administering an amount of cytolytic T cells, which are specific for the complexes of the HLA molecule and the peptide, to the subject wherein the amount of CTLs is sufficient to alleviate the disorder.

This invention also relates to methods for monitoring or detecting CTLs in a sample that are specific for a complex of the peptides of this invention, particularly SEQ ID NO: 1, SEQ ID NO: 2, SEQ ID NO:3, SEQ ID NO: 5, SEQ ID NO: 77, SEQ ID NO: 78, SEQ ID NO: 88, SEQ ID NO: 89, SEQ ID NO: 106, SEQ ID NO: 107 or SEQ ID NO: 111 and an HLA molecule, e.g., HLA-A2, HLA-B57 or HLA-B44 molecule. One method for detecting a CTL specific for a such complexes may comprise: (a) contacting a cytolytic T cell-containing sample with a composition comprising cells presenting a complex of the HLA molecule, e.g. an HLA-A2, HLA-B57 or HLA-B44 molecule, and the isolated peptide and (b) determining if a CTL in the CTL containing sample recognizes the cells presenting the complex of HLA and the isolated peptide, wherein recognition of the complex indicates the presence of a CTL specific for that complex. Recognition of the complex by a CTL may be manifested by lysis of the presenting cells, proliferation of CTLs in the sample or by release of TNFα by CTLs in the sample. The CTL containing sample may be from a subject having, or suspected of having, a disorder characterized by the presentation of the peptide/HLA complexes on the surfaces of cells associated with the disorder.

The cells which express the HLA/peptide complex on their surfaces may be transfected or transformed with a nucleic acid molecule which encodes the peptide. Alternatively, the cells may be transfected with a single expression vector comprising a nucleic acid molecule that encodes the peptide and a nucleic acid molecule that encodes the HLA molecule, e.g. an HLA-A2, HLA-B57 or HLA-B44 molecule. Alternatively the cells may be transfected with separate expression vectors encoding the HLA molecule or the peptide.

Another aspect of this invention are polytopes comprising one or more of the peptides of this invention. Polytopes are groups of two or more potentially immunogenic or immune stimulating peptides, which can be joined together in various ways, to determine if this type of molecule will stimulate and/or provoke an immune response. Preferably the polytope comprises a peptide consisting of the amino acid sequence set forth in SEQ ID NO: 1, SEQ ID NO: 2, SEQ ID NO: 3, SEQ ID NO: 5, SEQ ID NO: 77, SEQ ID NO: 78, SEQ ID NO: 88, SEQ ID NO: 89, SEQ ID NO: 106, SEQ ID NO: 107 or SEQ ID NO: 111, or the polytope comprises a peptide consisting of the amino acid sequence set forth in SEQ ID NO: 1, a peptide consisting of the amino acid sequence set forth in SEQ ID NO: 2, and a peptide consisting of the amino acid sequence set forth in SEQ ID NO: 3, a peptide consisting of the amino acid sequence set forth in SEQ ID NO: 5, a peptide consisting of the amino acid sequence set forth in SEQ ID NO: 77, a peptide consisting of the amino acid sequence set forth in SEQ ID NO: 78, a peptide consisting of the amino acid sequence set forth in SEQ ID NO: 88, a peptide consisting of the amino acid sequence set forth in SEQ ID NO: 89, a peptide consisting of the amino acid sequence set forth in SEQ ID NO: 106, a peptide consisting of the amino acid sequence set forth in SEQ ID NO: 107 and a peptide consisting of the amino acid sequence set forth in SEQ ID NO: 111.

Also a part of the invention are so-called "minigenes," i.e., nucleic acid molecules consisting of a nucleotide sequence that encodes the peptide of interest. The peptides of this invention are of a length that permits simple construction of all degenerate nucleotide sequences that encode the epitope of interest. The nucleic acid molecules consisting of these degenerate nucleotide sequences are also part of this invention and can be made a part of an extended "polytopic" sequence, using methods well known in the art, and can be incorporated into coding vectors where the minigene or genes of interest are operably linked to a promoter, for expression in a host cell.

The minigenes can also be used in concert with nucleotide sequences that encode an HLA molecule of interest, such as HLA-A2, HLA-B57 or HLA-B44, coding sequence. The two sequences can constitute part of a single vector, or a pair of vectors, which are then used in a kit or some other combination that permits the skilled artisan to use them to stimulate a T cell response, and so forth.

Similarly, one can envision treatment methods that employ dendritic cells, pulsed with the peptides of this invention, as well as cells which have been treated so as to present relevant complexes on their surfaces, see for example U.S. Pat. No. 6,251,603 issued Jun. 26, 2001 incorporated herein by reference. Such cells may be transformed or transfected with a tumor rejection antigen precursor TRAP gene, e.g., MAGE-C2 or a TRAP "minigene" or "minigenes", which encodes only relevant HLA-binding peptides such as tumor rejection antigens, and/or may be transfected or transformed with a relevant HLA-molecule encoding sequence, such as HLA-A2, HLA-B57 or HLA-B44. If appropriate, such cells may be irradiated prior to administration.

Also an aspect of this invention are "functional variants" of the peptides of this invention, particularly functional variants of the MAGE-C2 HLA class I-binding peptide consisting of the sequence set forth in SEQ ID NO: 1, 2, 3, 5, 77, 78, 88, 89, 106, 107 or 111. As used herein, a "functional variant" or "variant" of the peptides of this invention, particularly a peptide consisting of the sequence set forth in SEQ ID NO: 1, 2, 3, 5, 77, 78, 88, 89, 106, 107 or 111 is a peptide which contains one or more modifications to the primary amino acid sequence of the peptide, and yet has similar HLA class I and T cell receptor binding properties as compared to the unmodified peptide. The modifications may be an alteration in the amino acid sequence of the peptide such that the sequence differs from the unmodified peptide and yet the variant has similar HLA binding properties and a similar ability to induce a CTL response. The modifications may also be a chemical modification of the peptide, e.g., a moiety may be added to either end of the peptide to inhibit proteolytic degradation or a peptidic bond may be altered to enhance resistance to proteolysis. A further aspect of this invention are nucleic acid molecules which encode the functional variants, expression vectors comprising the nucleic acid molecules encoding the variants and to the cells transformed or transfected with a

DETAILED DESCRIPTION OF THE INVENTION

This invention relates to peptides of MAGE-C2, particularly peptides consisting of an amino acid sequence selected from the group consisting of SEQ ID NO: 1, SEQ ID NO: 2, SEQ ID NO: 3 (which is SEQ ID NO: 1 wherein X is an valine), or SEQ ID NO: 5 (which is SEQ ID NO: 1 wherein X is alanine), SEQ ID NO SEQ ID NO: 88, SEQ ID NO: 77 (which is SEQ ID NO: 88 wherein X is leucine), SEQ ID NO: 78 (which is SEQ ID NO: 88 wherein X is absent), SEQ ID NO: 89, SEQ ID NO: 106, SEQ ID NO: 107, and SEQ ID NO: 111. The peptides may be produced synthetically using standard techniques known in the art e.g., manufactured by good manufactorial practice guidelines (Multiple Systems, San Diego), or may be produced recombinantly using an expression vector that comprises a nucleic acid molecule that encodes the peptide in operable linkage with a promoter.

This invention also relates to nucleic acid molecules encoding the peptides of this invention. Oligonucleotides encoding the peptides of this invention can be easily prepared using methods that are standard in the art. Expression vectors comprising the isolated nucleic acid molecule of this invention in operable linkage with a promoter are also contemplated herein. The expression vector may be any that is known in the art, e.g., a plasmid, a cosmid, a bacteriophage or a viral vector. The nucleic acid molecule may be operatively linked to any promoter known in the art. Those of skill in the art are well-versed in recombinant DNA technologies and would appreciate that many different promoters are available and the choice of promoter should be one that is compatible with a particular host environment.

Also a part of this invention are host cells transformed or transfected with the nucleic acid molecules and expression vectors of this invention. Host cells may be any that are used routinely in the art, e.g. bacterial cells, e.g., E. coli, insect cells, mammalian cells, e.g., mouse, hamster, rat, cat, dog, horse, pig, monkey or human, avian cells, e.g., chicken, duck or goose, or plant cells, e.g. soy bean, tobacco, rice, wheat or corn. Methods for the transformation or transfection of particular host cells are well known in the art and need not be described in detail herein.

The peptides of this invention may be incorporated into polytopes. Two or more peptides of this invention can be joined together directly, or via the use of flanking sequences. See Thompson et al., *Proc. Natl. Acad. Sci. USA* 92(13): 5845-5849 (1995), teaching the direct linkage of relevant epitopic sequences. The use of polytopes as vaccines is well known. See, e.g. Gilbert et al., *Nat. Biotechnol.* 15(12): 1280-1284 (1997); Thomson et al., supra; Thomson et al., *J. Immunol.* 157(2): 822-826 (1996); Tam et al., *J. Exp. Med.* 171(1): 299-306 (1990), all of which are incorporated by reference. The Tam reference in particular shows that polytopes, when used in a mouse model, are useful in generating both antibody and protective immunity. Further, the reference shows that the polytopes, when digested, yield peptides which can be and are presented by HLAs. Tam demonstrates this by showing recognition of individual epitopes processed from polytope 'strings' via CTLs. This approach can be used, e.g., in determining how many epitopes can be joined in a polytope and still provoke recognition and also to determine the efficacy of different combinations of epitopes. Different combinations may be 'tailor-made' for patients expressing particular subsets of tumor rejection antigens. These polytopes can be introduced as polypeptide structures, or via the use of nucleic acid delivery systems. To elaborate, the art has many different ways available to introduce DNA encoding an individual epitope, or a polytope such as is discussed supra. See, e.g., Allsopp et al., *Eur. J. Immunol.* 26(8); 1951-1959 (1996), incorporated by reference. Adenovirus, pox-virus, Ty-virus like particles, plasmids, bacteria, etc., can be used. One can test these systems in mouse models to determine which system seems most appropriate for a given, parallel situation in humans. They can also be tested in human clinical trials.

The peptides of this invention either alone or in complex with an HLA molecule, particularly HLA-A2, HLA-B57 or HLA-B44, are useful for inducing an immune response in a subject, either humoral or cellular. The peptides may induce an immune response that may be either protective, diagnostic or therapeutic. The methods for inducing an immune response in a subject comprise administering a composition comprising an amount of a peptide of this invention in an amount that is sufficient to induce an immune response. The composition may comprise complexes of the inventive peptides and an HLA molecule, or e.g., the composition may comprise cells which present the peptides in complex with an HLA molecule. Methods for immunizing a subject with a composition are well known in the art, see e.g., Jager et al. *PNAS* 97(9): 12198-12203 (Oct. 24, 2000) incorporated herein by reference. The composition may comprise one or more additional peptides that bind to HLA molecules. The additional peptide may be one that binds to a Class I or a Class II major histocompatibility molecule (MHC).

If cells presenting a complex the HLA and the inventive peptides are administered to a subject, they should be cells that do not have harmful effects on the subject, e.g., the cells may be irradiated to insure they do not proliferate or the cells may be non-tumorigenic. The cells expressing the HLA/peptide may be autologous and may be transfected with a nucleic acid molecule that encodes the peptide. If the presenting cells do not naturally express a particular HLA molecule, e.g. HLA-A2, HLA-B57 or HLA-B44, the cells may also be transfected with a nucleic acid molecule that encodes the HLA. Alternatively the presenting cells may be transfected with a nucleic acid molecule that encodes both the peptide and HLA molecule. Likewise the polytopes and peptide analogs of this invention, which form complexes with the HLA that are recognized by the CTLs that recognize complexes of the HLA and a peptide having an amino acid sequence of SEQ ID NO: 1, SEQ ID NO: 2, SEQ ID NO: 3, SEQ ID NO: 5, SEQ ID NO: 77, SEQ ID NO: 78, SEQ ID NO: 88, SEQ ID NO: 89, SEQ ID NO: 106, SEQ ID NO: 107 or SEQ ID NO: 111, may also be used to induce an immune response in a subject, preferably a subject with a disorder characterized by the presentation of an HLA and a peptide having the amino acid sequence set forth in SEQ ID NO: 1, SEQ ID NO: 2, SEQ ID NO: 3, SEQ ID NO: 5, SEQ ID NO: 77, SEQ ID NO: 78, SEQ ID NO: 88, SEQ ID NO: 89, SEQ ID NO: 106, SEQ ID NO: 107 or SEQ ID NO: 111, For example the subject may have a cancer, or suspected of having cancer, wherein the cancer cells express the HLA/peptide complex on their surfaces.

Compositions which comprise the peptides, peptide analogs, polytopes, tetramer complexes or CTLs of this invention may further comprise a carrier, and/or an adjuvant. The carrier and adjuvant may be any that are routinely used in the art and are pharmaceutically acceptable, e.g., the carrier may be DMSO and the adjuvant may be GM-CSF or IL-12. A pharmaceutically or therapeutically acceptable or suitable carrier is preferably one that does not interfere with the effectiveness of the biological activity of the active components and which is not toxic to the subject.

The immunogenicity of peptides may be assayed by a variety of methods routinely used by one of skill in the art, see e.g., Jager et al. *PNAS*, 97(9):4760-4765 (Apr. 25, 2000) incorporated herein by reference and Jager et al., (Oct. 24, 2000) supra. The immunogenicity may be assayed in vitro by their ability to stimulate peripheral blood lymphocytes that are positive for the desired HLA molecule, e.g., HLA-A2, HLA-B57 or HLA-B44. The peripheral blood lymphocytes are preferably from healthy HLA-A2, HLA-B57 or HLA-B44 donors. Many assays are known in the art for determining if a CTL cell is stimulated by a cell that is presenting an HLA/peptide complex, e.g., ELISPOT, cytotoxicity assays and DTH assays (Jager et al. (April 2000) supra and Jager et al. (October 2000) supra). When a CTL cell recognizes a particular HLA-peptide complex it is activated and this activation is manifested by, e.g., CTL proliferation, lysis of cells presenting a complex of HLA, e.g., HLA-A2, HLA-B57 or HLA-B44, and the peptide by the activated CTL, and release of cytokines by the activated CTLs. The release of cytokines may be assayed by e.g., ELISPOT. The activation of the CTLs may also be detected by admixing the CTL cell containing sample with a tetramer, as described supra, that is composed of a the peptide of this invention, an HLA molecule, particularly an HLA-A2, HLA-B57 or HLA-B44 molecule, a $\beta_2$-microglobulin and biotin, which may then be labeled with a molecule such as e.g. avidin or streptavidin (see U.S. application Ser. No. 09/725,993, incorporated herein by reference, for a description of the generation and use of such tetramers.) Preferably the tetramer comprises HLA-A2, HLA-B57 or HLA-B44, a peptide of this invention, particularly a peptide consisting of the sequence set forth in SEQ ID NO: 1, SEQ ID NO: 2, SEQ ID NO: 3, SEQ ID NO: 5, SEQ ID NO: 77, SEQ ID NO: 78, SEQ ID NO: 88, SEQ ID NO: 89, SEQ ID NO: 106, SEQ ID NO: 107 or SEQ ID NO: 111, and biotin. Such tetramers, as well as compositions comprising the tetramers and methods for their use are also aspects of this invention.

In a method for identifying T cells, such as CTLs which are specific for a peptide/HLA complex, where the peptide derives from a protein of interest, a sample believed to contain relevant CTLs is contacted to an antigen presenting cell, such as a dendritic cell, which has been infected with a first viral vector that encodes the protein of interest. Following this contact, the CTLs are then contacted with a second population of antigen presenting cells which have been, e.g., infected with a second viral vector which also encodes the protein of interest, where the second viral vector is different from the first viral vector. One benefit derived from this approach is that any immune response can be more refined in that it is targeted to the antigen rather than any aspect of the viruses. Preferably, the first viral vector is an adenovirus vector, preferably one that is non replicative, and the second vector is a vaccinia vector. It will be understood, however, that these may be reversed, and that only one of these two choices can be used, in combination with a second virus that differs from one of these two choices. The method requires an antigen presenting cell, such as a dendritic cell, or some other cell type capable of presenting complexes of an HLA molecule and a peptide on its surface. In practice, the method preferably involves the use of autologous cells, i.e., antigen presenting cells and CTLs from the same patient, but the method can be carried out with allogeneic cells as well. Use of the method permits one to identify epitopes that are restricted by their presenting HLA molecule.

The methods of this invention are particularly useful for detecting the presence of, and monitoring the proliferation of, CTLs in a cell sample taken from a subject having a disorder, or suspected of having a disorder, e.g., a cancer, associated with the presentation of complexes of HLA and a peptide having an amino acid sequence set forth in SEQ ID NO: 1, SEQ ID NO: 2, SEQ ID NO: 3, SEQ ID NO: 5, SEQ ID NO: 77, SEQ ID NO: 78, SEQ ID NO: 88, SEQ ID NO: 89, SEQ ID NO: 106, SEQ ID NO: 107 and SEQ ID NO: 111, on the surfaces of cells associated with that disorder, wherein the CTLs are specific for the complex an HLA molecule, e.g. HLA-A2, HLA-B57 or HLA-B44, and a peptide having an amino acid sequence set forth in SEQ ID NO: 1, SEQ ID NO: 2, SEQ ID NO: 3, SEQ ID NO: 5, SEQ ID NO: 77, SEQ ID NO: 78, SEQ ID NO: 88, SEQ ID NO: 89, SEQ ID NO: 106, SEQ ID NO: 107 or SEQ ID NO: 111, The subject may be monitored for the generation and proliferation of CTLs by assaying cell samples from the subject at various times to determine the number of CTLs that are specific for a particular complex of the HLA and peptide and to determine if that number is increasing or decreasing over time. In particular, the peptide of this invention may be administered to the subject and then the subject may be monitored for a response by CTLs and for their subsequent proliferation. The peptide may be administered to the subject in a form where it is not in complex with an HLA molecule or it may be administered in complex with the HLA molecule, particularly HLA-A2, HLA-B57 or HLA-B44. The peptide may be administered with any pharmaceutically suitable carrier, and may also be administered with a pharmaceutically acceptable adjuvant, e.g., GM-CSF or IL-12. Intact cells or cell parts that present the complex of HLA and peptide on their surface may be administered to the subject in a pharmaceutically acceptable carrier. The method is particularly useful for a subject who has cancer cells that express a MAGE, particularly MAGE-C2, and particularly one whose cells express HLA-A2, HLA-B57 or HLA-B44 as well.

CTLs per se that are specific for a complex of an HLA, particularly HLA-A2, HLA-B57 or HLA-B44, and a peptide having an amino acid sequence as set forth in SEQ ID NO: 1, SEQ ID NO: 2, SEQ ID NO:3, SEQ ID NO: 5, SEQ ID NO: 77, SEQ ID NO: 78, SEQ ID NO: 88, SEQ ID NO: 89, SEQ ID NO: 106, SEQ ID NO: 107 or SEQ ID NO: 111, are also an aspect of this invention. The CTLs are useful in adoptive transfer wherein the CTLs are administered to a subject in need thereof in an amount that is sufficient for the CTLs to recognize cells presenting the complex and lysing the cells. The CTLs are also useful for identifying cells that present complexes of HLA, e.g. HLA-A2, HLA-B57 or HLA-B44, and the peptides or peptide analogs of this invention.

This invention also relates to a method for treating a subject with a disorder characterized by the presence of complexes of an HLA molecule, e.g. HLA-A2, HLA-B57 or HLA-B44 molecules, and a peptide having an amino acid sequence consisting of an amino acid sequence selected from the group consisting of SEQ ID NO: 1, SEQ ID NO: 2, SEQ ID NO: 3, SEQ ID NO: 5, SEQ ID NO: 77, SEQ ID NO: 78, SEQ ID NO: 88, SEQ ID NO: 89, SEQ ID NO: 106, SEQ ID NO: 107 and SEQ ID NO: 111, on the surfaces of cells associated with the disorder. The method comprises administering to the subject an amount of cytolytic T cells, which are specific for complexes of the HLA molecules and the peptide, wherein the amount is sufficient to alleviate the disorder. The peptides, peptide analogs or polytopes may be administered to the subject in an amount that is sufficient to stimulate CTLs and alleviate the symptoms of the disorder.

Therapeutically or pharmaceutically effective amount as it is applied to the peptides, functional variants of the peptide, tetramers, compositions and CTLs of this invention refers to the amount of the peptides, functional variants of the peptides, tetramers, compositions and CTLs of this invention that is sufficient to induce a desired biological result. The biological result may be the alleviation of the signs, symptoms or causes of a disease, or any other desired alteration of a biological system. In the present invention that amount may be sufficient to induce an immune response such as the production of antibodies specific for the peptides or peptide analogs of this invention or a response by CTL cells, e.g., their proliferation or their lysis of target cells expressing an appropriate HLA/peptide complex, or sufficient to alleviate the symptoms of a disorder characterized by the expression of a complex of HLA, particularly HLA-A2, HLA-B57 or HLA-B44, and a peptide consisting of the amino acid sequence set forth in SEQ ID NO: 1, SEQ ID NO: 2, SEQ ID NO: 3, SEQ ID NO: 5, SEQ ID NO: 77, SEQ ID NO: 78, SEQ ID NO: 88, SEQ ID NO: 89, SEQ ID NO: 106, SEQ ID NO: 107 or SEQ ID NO: 111.

An analysis of other members of the MAGE family, e.g., MAGE-C1, A10, A11, B1, B3 and B4 reveal peptide sequences that are homologous to the ALKDVEERV MAGE-C2 peptide described herein. Table 1 presents several of these peptides, their amino acid sequence and ligation strength to HLA-A*0201.

TABLE 1

Mage-C2 Peptide Homologs

| Protein | Peptide | Ligation strength* | SEQ ID NO: |
|---------|---------|--------------------|------------|
| Mage-C2 | ALKDVEERV | 22 | 3 |
| Mage-C1 | ALKDVEERA | 16 | 5 |
| Mage-A10 | ALKDEEERA | 17 | 6 |
| Mage-A11 | ALREEGEGV | 25 | 7 |
| Mage-B1, -B4 | ALRDEEERA | 17 | 8 |
| Mage-B3 | ALRDEEERV | 23 | 9 |

*Ligation strength to HLA-A*0201 according to the SYFPEITHI database. (see, Rammensee et al., SYFPEITHI: database for MHC ligands and peptide motifs. Immunogenetics. 1999 November; 50(3-4): 213-9 and syfpeithi.bmi-heidelberg.com both incorporated herein by reference)

Interestingly, the MAGE-C1 and C2 peptides differ by only a single amino acid, i.e., the $9^{th}$ residue is valine in the MAGE-C2 peptide and alanine in the MAGE-C1 peptide. Thus, we predict that an HLA complex comprising the MAGE-C1 peptide will be recognized by the CTL clone 606 C/22.2. It has previously been shown that for the NY-ESO-1 tumor antigen a T-cell clone retained its recognition after an amino acid substitution at position 9 of the peptide.

Since the MAGE family are known antigens with appropriate tumor expression profiles it follows that homologous peptides derived from these antigens might also be recognized by T cells, as has been observed with other homologous MAGE peptides from Mage-A1 (EADPTGHSY SEQ ID NO: 10) and MAGE-A3 (EVDPIGHLY SEQ ID NO: 11), see U.S. Pat. No. 5,405,940.

A MAGE-C2 peptide (SEQ ID NO: 3) is naturally processed and presented by HLA-A2 on the surface of tumor cells and recognized by specific T cells. Thus it is expected that the homologous MAGE-C1 peptide (SEQ ID NO: 5) which has a single conservative substitution at the C-terminal residue (position 9), would also be presented by HLA-A2 and recognized by T cells. Gure et al. and Chen et al. infra demonstrate that some cancer patients display both a T cell response to MAGE-C2 (CT10) (SEQ ID NO: 71) or to MAGE-C1 (CT7) (SEQ ID NO: 73) and a humoral response to the proteins (Gure et al., *Int. J Canc.* 85:726-732 (2002) and Chen et al. *PNAS* 95(12):6919-6923 (1998) both incorporated herein by reference) demonstrating the strong immunogenic properties of the proteins. Based on the disclosure herein, we expect additional homologous peptides derived from other members of the MAGE family (SEQ ID No: 6 to 9, Table 1) to form HLA/peptide complexes that are targets for cytolytic T cells. As such the peptides disclosed in Table 1 and their use in diagnostic and therapeutic assays as disclosed herein are also a part of this invention.

An analysis of the peptide sequences listed in Table 1 identified an immunogenic motif, i.e., ALXXXXEXX (SEQ ID NO: 12) where the X's represent two alternative amino acids: X at position 3 is Arg (R) or Lys (K), X at position 4 is Asp (D) or Glu (E), X at position 5 is Val (V) or Glu (E), X at position 6 is Glu (E) or Gly (G), X at position 8 is Gly (G) or Arg (R) and X at position 9 is Ala or Val. A list of all 64 possible peptides is shown in Table 2.

TABLE 2

Possible peptides from the immunogenic motif. The MAGE-C2 peptide is indicated in bold italics and other peptides from Table 1 are indicated with italics.

| Peptide | SEQ ID NO |
|---------|-----------|
| ALRDVEERV | 13 |
| ALRDVEERA | 14 |
| ALRDVEEGA | 15 |
| ALRDVEEGV | 16 |
| ALRDVGERV | 17 |
| ALRDVGERA | 18 |
| ALRDVGEGA | 19 |
| ALRDVGEGV | 20 |
| *ALRDEEERV* | 9 |
| *ALRDEEERA* | 8 |
| ALRDEEEGA | 21 |
| ALRDEEEGV | 22 |
| ALRDEGERV | 23 |
| ALRDEGERA | 24 |
| ALRDEGEGA | 25 |
| ALRDEGEGV | 26 |
| ALREVEERV | 27 |
| ALREVEERA | 28 |
| ALREVEEGA | 29 |
| ALREVEEGV | 30 |
| ALREVGERV | 31 |
| ALREVGERA | 32 |
| ALREVGEGA | 33 |
| ALREVGEGV | 34 |
| ALREEEERV | 35 |
| ALREEEERA | 36 |
| ALREEEEGA | 37 |
| ALREEEEGV | 38 |
| ALREEGERV | 39 |
| ALREEGERA | 40 |
| ALREEGEGA | 41 |
| *ALREEGEGV* | 7 |
| *ALKDVEERV* | 3 |
| ALKDVEERA | 5 |
| ALKDVEEGA | 42 |
| ALKDVEEGV | 43 |
| ALKDVGERV | 44 |
| ALKDVGERA | 45 |
| ALKDVGEGA | 46 |
| ALKDVGEGV | 47 |
| ALKDEEERV | 48 |
| *ALKDEEERA* | 6 |
| ALKDEEEGA | 49 |
| ALKDEEEGV | 50 |
| ALKDEGERV | 51 |
| ALKDEGERA | 52 |
| ALKDEGEGA | 53 |
| ALKDEGEGV | 54 |
| ALKEVEERV | 55 |
| ALKEVEERA | 56 |
| ALKEVEEGA | 57 |
| ALKEVEEGV | 58 |
| ALKEVGERV | 59 |
| ALKEVGERA | 60 |
| ALKEVGEGA | 61 |

TABLE 2-continued

Possible peptides from the immunogenic motif. The MAGE-C2 peptide is indicated in bold italics and other peptides from Table 1 are indicated with italics.

| Peptide | SEQ ID NO |
|---|---|
| ALKEVGEGV | 62 |
| ALKEEEERV | 63 |
| ALKEEEERA | 64 |
| ALKEEEEGA | 65 |
| ALKEEEEGV | 66 |
| ALKEEGERV | 67 |
| ALKEEGERA | 68 |
| ALKEEGEGA | 69 |
| ALKEEGEGV | 70 |

Recent analysis suggests that homologous peptides which bind to more than one HLA molecules will induce a T cell response. This has been demonstrated for the MAGE-A1 (EADPTGHSY SEQ ID NO: 10) and MAGE-A3 (EVD-PIGHLY SEQ ID NO: 1) peptides and the HLA molecule HLA-A1 and HLA-B35, see U.S. Pat. No. 5,405,940, Schultz E. et al. *Tissue Antigens*. 2001 February; 57(2):103-9 and Luiten R. et al. *Tissue Antigens*. 2000 July; 56(1):77-81 all incorporated herein by reference. Thus the peptide(s) in Table 1 which bind to other HLA molecules in addition to HLA-A2, such as HLA-A1, A3, A26, B7, B8, B15, B27, B44, or B51 are likely to be peptides that stimulate a CTL response. Methods for determining if a peptide binds to a particular HLA molecule are well known in the art.

Also an aspect of this invention are "functional variants" of the peptides of this invention, particularly functional variants of the MAGE-C2 HLA class I-binding peptide consisting of the sequence set forth in SEQ ID NO: 1, 2, 3, 5, 77, 78, 88, 89, 106, 107 or 111. As used herein, a "functional variant" or "variant" of the peptides of this invention, particularly a peptide consisting of the sequence set forth in SEQ ID NO: 1, 2, 3, 5, 77, 78, 88, 89, 106, 107 or 111 is a peptide which contains one or more modifications to the primary amino acid sequence of an unmodified peptide, and yet has similar HLA class I and T cell receptor binding properties as compared to the unmodified peptide. Thus another aspect of this invention is the modification of MAGE-C2 HLA class I binding peptides to generate variants which have, e.g., (1) an enhanced stability in a preselected expression system or enhanced stability of protein-protein binding, such as HLA-peptide binding, as compared to the unmodified peptide; (2) a novel activity or property, e.g., a variant of a MAGE-C2 HLA class I-binding peptide which contains an antigenic epitope or a detectable moiety; or (3) a different amino acid sequence as compared to the unmodified peptide yet displays the same or similar T cell stimulatory properties as the unmodified MAGE-C2 HLA class I-binding peptide. Modified MAGE-C2 HLA class I binding peptides can be obtained by mutating a nucleic acid molecule that encodes the unmodified form of the peptide by e.g., introducing deletions, point mutations, or insertions, which result in a truncated peptide, or a peptide having an altered amino acid sequence, e.g., deletions, insertions or substitutions of one or more amino acids as compared to the unmodified peptide. Alternatively, modified MAGE-C2 HLA-class I binding peptides can be generated by directly modifying the peptide, e.g., by cleaving the peptide, adding a linker molecule, adding a detectable moiety, e.g., biotin, adding a fatty acid, substituting one amino acid for another and the like. Variants of the peptides also embrace fusion proteins comprising all or part of the MAGE-C2 HLA class I binding peptide amino acid sequence and a fusion partner.

The variants of the peptides include for example, peptides that do not have the sequence set forth in SEQ ID NO: 1, SEQ ID NO: 2, SEQ ID NO: 3, SEQ ID NO: 5, SEQ ID NO: 77, SEQ ID NO: 78, SEQ ID NO: 88, SEQ ID NO: 89, SEQ ID NO: 107 or SEQ ID NO: 111, and yet form complexes with HLA molecules, particularly an HLA-A2, HLA-B57 or HLA-B44 molecule, and stimulate cytolytic T cells (CTLs) that are specific for complexes of the HLA and a peptide consisting of an amino acid sequence selected from the group consisting of SEQ ID NO: 1, SEQ ID NO: 2, SEQ ID NO: 3, SEQ ID NO: 5, SEQ ID NO: 77, SEQ ID NO: 78, SEQ ID NO: 88, SEQ ID NO: 89, SEQ ID NO: 106, SEQ ID NO: 107 and SEQ ID NO: 111. The peptides may be, e.g., from 8-11 amino acids in length and preferably comprise at least 8 contiguous amino acids of the sequences set forth in SEQ ID NO: 1, SEQ ID NO: 2, SEQ ID NO: 3, SEQ ID NO: 5, SEQ ID NO: 77, SEQ ID NO: 78, SEQ ID NO: 88, SEQ ID NO: 89, SEQ ID NO: 106, SEQ ID NO: 107 or SEQ ID NO: 111.

The amino acid sequence of MAGE-C2 HLA class I binding peptides may be of natural or non-natural origin, that is, they may comprise a natural MAGE-C2 HLA class I binding peptide molecule or may comprise a modified sequence as long as the amino acid sequence retains the ability to stimulate T cells when presented and retains the property of binding to an HLA class I molecule such as an HLA-A2, HLA-B57 or HLA-B44 molecule. For example, MAGE-C2 HLA class I binding peptides in this context may be fusion proteins of a MAGE-C2 HLA class I binding peptide and unrelated amino acid sequences, synthetic peptides of amino acid sequences of MAGE C2 set forth in SEQ ID NO: 71 or the MAGE-C2 peptides sequences set forth in SEQ ID NO: 3, SEQ ID NO: 77 and SEQ ID NO: 107, labeled peptides, peptides isolated from patients with a MAGE-C2 expressing cancer, peptides isolated from cultured cells which express MAGE-C2, peptides coupled to nonapeptide molecules (for example in certain drug delivery systems) and other molecules which include the amino acid sequences of the MAGE-C2 peptides set forth in SEQ ID NO: 3 and SEQ ID NO: 77 and SEQ ID NO: 107.

Preferably, MAGE-C2 HLA class I binding peptides are non-hydrolyzable. To provide such peptides, one may select MAGE-C2 HLA class I binding peptides from a library of non-hydrolyzable peptides, such as peptides containing one or more D-amino acids or peptides containing one or more non-hydrolyzable peptide bonds linking amino acids. Many non-hydrolyzable peptide bonds are known in the art, along with procedures for synthesis of peptides containing such bonds. Non-hydrolyzable bonds include $\Psi(CH_2NH)$-reduced amide peptide bonds, $\Psi(COCH_2)$-ketomethylene peptide bonds $\Psi(CH(CN)NH)$-(cyanomethylene)amino peptide bonds, $\Psi(CH_2CH(OH))$-hydroxyethylene peptide bonds, $\Psi(CH_2O)$-peptide bonds, and $\Psi(CH_2S)$-thiomethylene peptide bonds. Methods for determining such functional variants are provided in U.S. Pat. No. 6,087,441, incorporated herein by reference.

Among the variants having a change in an amino acid of MAGE-C2 set forth in SEQ ID No: 71 or the MAGE-C2 peptides set forth in SEQ ID NO: 3, SEQ ID NO: 77, or SEQ ID NO: 107, functional variants of the MAGE-C2 HLA class I binding peptide having conservative amino acid substitutions are preferred, i.e., substitutions which retain a property of the original amino acid such as charge, hydrophobicity, conformation, etc. Examples of conservative substitutions of amino acids include substitutions made amongst amino acids within the following groups: (a) Met, Ile, Leu, Val; (b) Phe, Tyr, Trp; (c) Lys, Arg, His; (d) Ala, Gly; (e) Ser, Thr; (f) Gln, Asn; and (g) Glu, Asp.

The peptides of this invention may be chemically modified with protective groups at one or both ends, or one or more peptide bonds may be replaced with non-peptide bonds to produce variants that are less susceptible to proteolytic cleavage than the non-modified peptides. For example, one or more peptide bonds may be replaced with an alternative type of covalent bond (e.g., a carbon-carbon bond or an acyl bond). Where proteolytic degradation of the peptide following administration to a subject is a problem, the sensitive peptide bonds may be replaced to increase the stability of the peptide and increase its usefulness as a therapeutic. Peptidase sensitive bonds may be determined by standard methods, see for example, application 60/290,646 incorporated herein by reference. Methods of incorporating various types of bonds into peptides, are well known in the art and need not be described in detail here. Peptide analogs may also be generated by incorporating amino-terminal or carboxyl terminal blocking groups such as t-butyloxycarbonyl, acetyl, alkyl, succinyl, methoxysuccinyl, suberyl, adipyl, azelayl, dansyl, benzyloxycarbonyl, fluorenyl methoxycarbonyl, methoxyazelayl, methoxyadipyl, methoxysuberyl, and 2,4-dinitrophenyl, thereby rendering the peptide analog or mimetic less susceptible to proteolysis. Non-peptide bonds and carboxyl- or amino-terminal blocking groups can be used singly or in combination to render the peptide analog less susceptible to proteolysis than the corresponding peptide. Peptide with modifications such as β-a.a. (β-amino acid), d-a.a., Me-a.a. or αNMe-a.a. may be synthesized by incorporation of a corresponding modified amino acid. Many modified amino acids are commercially available (see, e.g., Bachem A G, Budendorf, Switzerland (NMe-a.a.), Fluka Chemie GmbH, Bush, Switzerland (α-a.a.), Acros Organic France, Noisy-Le-Grand, France (dMe-a.a). Me amino acid are often sold in a racemic form, and as a consequence, peptides with Me modification may also be produced in a racemic form.

The peptides of this invention may comprise a modification such as for example a methylation of an carboxy group (Me-peptide) methylation of a nitrogen engaged in peptidic bond formation (NMe-peptide), acetylation of a terminal nitrogen (acetyl peptide), amidation of a terminal carboxylic group (amide-peptide), reduced bond ($\Psi$1-2($CH_2$—NH), β-amino acid (aa), e.g., β-alanine, β-glutamic acid, D-amino acid (d-aa), hydroxylation of a terminal nitrogen (NOH-peptide), retro-inverso peptide bond ($\Psi$1-2(CO—$NH_2$), and cyclic amino acid, e.g., pyro-glutamic a.a. See e.g., U.S. patent application Ser. No. 09/114,002 filed Jul. 10, 1998 and incorporated herein by reference for examples of methods for modifying peptides to increase their resistance to proteolytic cleavage and for assays of peptide stability. A reduced bond $\Psi(CH_2$—NH) can be formed by the reductive alkylation of a free amino group with a Fmoc protected amino aldehyde performed according to the method developed by Fehrentz and Castro (Fehrentz and Castro, *Synthesis*, 676-678 (1983) incorporated herein by reference). Peptides may be purified by reverse-phase high-pressure liquid chromatography (RP-HPLC) on a C8 column (Aquapore (Brownlee)). Identity of the purified peptides can be confirmed by mass spectrometry using electrospray ionisation (ESI-MS). Peptide stock solutions may be adjusted to appropriate peptide concentration in, e.g., 100% dimethylsulfoxide (DMSO), and stored at −20° C. N-terminal-hydroxy peptides can be synthesized according to methods disclosed in e.g., Bianco et al., *J. Peptide Sci.*, 4: 471-478 (1998), Guichard et al., *J. Med. Chem.*, 39: 2030-2039 (1996) and Dürr et al., *Angew. Chem. Int. Ed. Engl.*, 31(6): 785-787 (1992), all incorporated herein by reference. The peptides of this invention may be synthesized by any method known in the art, e.g. the solid-phase method using the Fmoc chemistry and DIPC/HOAt (N,N diisopropylcarbodiimmide/N-hydroxyazabenzothiazole) coupling procedure.

Methods for identifying functional variants of the MAGE-C2 HLA class I binding peptides are provided in a U.S. Pat. Nos. 6,277,956 and 6,326,200 and published PCT application WO0136453 and U.S. application Ser. Nos. 09/440,621, 09/514,036, 09/676,005 all incorporated herein by reference. In general, the methods include selecting an unmodified MAGE-C2 HLA class I binding peptide, an HLA class I binding molecule which binds the MAGE-C2 HLA class I binding peptide, and a T cell which is stimulated by the unmodified MAGE-C2 HLA class I binding peptide presented by the HLA class I binding molecule. Preferably, the unmodified MAGE-C2 HLA class I binding peptide comprises the amino acid sequence of SEQ ID NO: 1, SEQ ID NO: 88 or SEQ ID NO: 107. More preferably, the unmodified peptide consists of the amino acid sequence set forth in SEQ ID NO: 3, SEQ ID NO: 77 or SEQ ID NO: 107. A first amino acid residue of the MAGE-C2 HLA class I binding peptide is mutated to prepare a modified peptide. Any method for preparing modified peptides can be employed, such as chemical synthesis of the modified peptide, recombinantly producing the modified peptide using a mutated nucleic acid molecule, and the like.

The binding of a modified peptide to HLA class I binding molecule and the stimulation of a T cell are then determined according to standard procedures wherein binding of the variant peptide to the HLA class I binding molecule and stimulation of the T cell by the variant peptide presented by the HLA class I binding molecule indicates that the variant peptide is a functional variant. For example, the peptide to be assayed can be contacted with an antigen presenting cell, which contains the HLA class I molecule known to bind to a particular MAGE-C2 peptide, to form a complex of the modified peptide and the HLA class I molecule. The cells presenting this complex can then be contacted with a T cell that recognizes a complex of the particular unmodified MAGE-C2 peptide and the HLA class I binding molecule. Such T cells can be obtained from a patient having a condition characterized by expression of MAGE-C2. Recognition of the complex of modified peptide and HLA class I molecule by the T cells can be determined by measuring any indicator of T cell stimulation known in the art. Binding of the modified peptide to the HLA class I binding molecule and stimulation of the T cell by the modified peptide presented by the HLA class I binding molecule indicates that the modified peptide is a functional variant.

It is also possible to evaluate the effectiveness of the functional variant on the stimulation of T cells by comparing the stimulation of the T cell by complexes of the HLA and unmodified peptide with the stimulation of the T cell by complexes of HLA and the functional variant. By comparing the stimulation levels, peptides with increased T cell stimulatory properties can be identified.

Variants of the MAGE-C2 HLA class I binding peptides prepared by any of the foregoing methods can be sequenced, if necessary, using standard techniques to determine the amino acid sequence and thus deduce the nucleotide sequence which encodes such variants.

Also an aspect of this invention are combinatorial libraries of modified peptides which are screened for variants of peptides having an amino acids of the sequences set forth in SEQ ID NO: 1, SEQ ID NO: 2, SEQ ID NO: 3, SEQ ID NO: 5, SEQ ID NO: 77, SEQ ID NO: 78, SEQ ID NO: 88, SEQ ID NO: 89, SEQ ID NO: 106, SEQ ID NO: 107 or SEQ ID NO: 111. The modified peptides may be generated by the systematic substitution, deletion or modification of one or more amino acids of the sequences set forth in SEQ ID NO: 1, SEQ ID NO: 2, SEQ ID NO: 3 or SEQ ID NO: 5, SEQ ID NO: 77, SEQ ID NO: 78, SEQ ID NO: 88, SEQ ID NO: 89, SEQ ID NO: 106, SEQ ID NO: 107 or SEQ ID NO: 111.

The peptides and libraries may be constructed using well known methods. See, e.g., Merrifield, R. B., "Solid phase peptide synthesis. I. The synthesis of a tetrapeptide", *J. Am. Chem. Soc.* 85:2149-2154 (1963); M. Bodanszky, "Principles of Peptide Synthesis", *Springer-Verlag* p. 21-27 (1984); Jung et al., "Multiple Peptide Synthesis Methods and Their Applications" *Angew. Chem. Int. Ed. Engl.*, vol. 31, No. 4, pp. 367-383 (April 1992); Janda, K. D., "Tagged versus untagged libraries: Methods for the generation and screening of combinatorial chemical libraries", *Proc. Natl. Acad. Sci. USA*, vol. 91, pp. 10779-10785 (November 1994), and Barbas et al., *Phage Display: A Laboratory Manual*, Cold Spring Harbor Laboratory Press, Cold Spring Harbor N.Y. (2001) (all incorporated herein by reference). For example, oligonucleotides that encode modified peptides may be generated by synthesizing oligonucleotides using mixtures of two or more of the four nucleoside triphosphates rather than pure preparations of the nucleoside triphosphates. The mixtures of nucleosides introduce changes into the oligonucleotide sequence and these changed oligonucleotides encode modified peptides that differ in only a few residues from the initial peptide. Libraries of modified peptides may also be prepared, for example, by using a pIII or a pVIII based peptides on phage system, and combinatorial libraries can be screened to identify a phage that presents a variant that binds to an HLA molecule and the DNA of the phage screened to determine the sequence of the variant displayed on the surface of the phages. Additional methods for generating libraries of peptides are also disclosed in, e.g., U.S. Pat. No. 5,932,546, incorporated herein by reference.

A combinatorial library of the modified peptides may be screened for functional variant having, e.g., the following characteristics: a peptide that does not consist of the sequence set forth in SEQ ID NO: 1, SEQ ID NO: 2, SEQ ID NO: 3 or SEQ ID NO: 5, SEQ ID NO: 77, SEQ ID NO: 78, SEQ ID NO: 88, SEQ ID NO: 89, SEQ ID NO: 106, SEQ ID NO: 107 or SEQ ID NO: 111, and yet binds to an HLA molecule, preferably HLA-A2 molecule, and when bound to the HLA molecule they form a complex that is recognized by a cytolytic T cell that recognizes a complex of the HLA molecule, preferably HLA-A2, HLA-B57 or HLA-B44, and a peptide selected from the group consisting of SEQ ID NO: 1, SEQ ID NO: 2, SEQ ID NO: 3 or SEQ ID NO: 5, SEQ ID NO: 77, SEQ ID NO: 78, SEQ ID NO: 88, SEQ ID NO: 89, SEQ ID NO: 106, SEQ ID NO: 107 or SEQ ID NO: 111. Such functional variants are useful in the methods of this invention, e.g., for stimulating CTL cells that recognize cells presenting a complex of an HLA molecule e.g. HLA-A2, HLA-B57 or HLA-B44 and a peptide selected from the group consisting of SEQ ID NO: 1, SEQ ID NO: 2, SEQ ID NO: 3 or SEQ ID NO: 5, SEQ ID NO: 77, SEQ ID NO: 78, SEQ ID NO: 88, SEQ ID NO: 89, SEQ ID NO: 106, SEQ ID NO: 107 or SEQ ID NO: 111.

Also a part of this invention are antibodies, e.g., polyclonal and monoclonal, and antibody fragments, e.g. Fab, Fab', Fab'-SH, F(ab'), and Fv fragments, diabodies and any antibody fragment that is a polypeptide having a primary structure consisting of one uninterrupted sequence of contiguous amino acid residues (single-chain antibody fragment or single chain polypeptide), including without limitation; single-chain Fv (scFv) molecules; single chain polypeptides containing only one light chain variable domain, or a fragment thereof that contains the three CDRs of the light chain variable domain, without an associated heavy chain moiety; and single chain polypeptides containing only one heavy chain variable region, or a fragment thereof containing the three CDRs of the heavy chain variable region, without an associated light chain moiety; and multi specific antibodies formed from antibody fragments, that specifically bind the peptides or HLA/peptide complexes disclosed herein. Preferably the antibodies, the antibody fragments and T cell receptors bind the HLA/peptide complexes in a peptide-specific manner. Such antibodies are useful, for example, in identifying cells presenting the HLA/peptide complexes, particularly complexes comprising an HLA-A2, A3, A26, HLA-B7, B8, B15, B27, B35, B44, B51, or B57 molecule, preferably HLA-A2, B57 or B44, and a peptide consisting essentially of the sequence set forth in SEQ ID NO: 1 (wherein X is Ala, Val, Leu, Ile, Pro, Phe, Met, Trp or Glu, preferably Val (SEQ ID NO: 3) or Ala (SEQ ID NO: 5)), 2, 3, 4, 5, 6, 7, 8, 9, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 77, 78, 88 (wherein X is absent (SEQ ID NO: 78) or any amino acid), 89, 106, 107 or 111. Preferably the peptide consists of the sequence set forth in SEQ ID NO: 1, SEQ ID NO: 2, SEQ ID NO: 3, SEQ ID NO: 5, SEQ ID NO: 77, SEQ ID NO: 78, SEQ ID NO: 88, SEQ ID NO: 89, SEQ ID NO: 106, SEQ ID NO: 107 or SEQ ID NO: 111.

Such antibodies are also useful in promoting the regression or inhibiting the progression of a tumor which expresses complexes of the HLA and peptide. Polyclonal antisera and monoclonal antibodies specific to the peptides or HLA/peptide complexes of this invention may be generated according to standard procedures. See e.g., Catty, D., *Antibodies, A Practical Approach*, Vol. 1, IRL Press, Washington D.C. (1988); Klein, *J. Immunology: The Science of Cell-Non-Cell Discrimination*, John Wiley and Sons, New York (1982); Kennett, R., et al., *Monoclonal Antibodies, Hybridoma, A New Dimension In Biological Analyses*, Plenum Press, New York (1980); Campbell, A., *Monoclonal Antibody Technology, in Laboratory Techniques and Biochemistry and Molecular Biology*, Vol. 13 (Burdon, R. et al. EDS.), Elsevier Amsterdam (1984); Eisen, H. N., *Microbiology*, third edition, Davis, B. D. et al. EDS. (Harper & Rowe, Philadelphia (1980); Kohler and Milstein, *Nature*, 256:495 (1975) all incorporated herein by reference.) Methods for identifying Fab molecules endowed with the antigen-specific, HLA-restricted specificity of T cells has been described by Denkberg et al. *Proc. Natl. Acad. Sci.* 99:9421-9426 (2002) and Cohen et al. *Cancer Research* 62:5835-5844 (2002) (both incorporated herein by reference). Methods for generating and identifying other antibody molecules, e.g., scFv and diabodies are well known in the art, see e.g., Bird et al., *Science*, 242:423-426 (1988); Huston et al., *Proc. Natl. Acad. Sci.*, 85:5879-5883 (1988); Mallender and Voss, *J. Biol. Chem.* 269:199-206 (1994); Ito and Kurosawa, *J Biol Chem* 27: 20668-20675 (1993), and; Gandecha et al., *Prot Express Purif.* 5: 385-390 (1994) (all incorporated herein by reference).

The antibodies of this invention can be used for experimental purposes (e.g. localization of the HLA/peptide complexes, immunoprecipitations, Western blots, flow cytometry, ELISA etc.) as well as diagnostic or therapeutic purposes, e.g., assaying extracts of tissue biopsies for the presence of HLA/peptide complexes, targeting delivery of cytotoxic or cytostatic substances to cells expressing the appropriate HLA/peptide complex. The antibodies of this invention are useful for the study and analysis of antigen presentation on tumor cells and can be used to assay for changes in the HLA/peptide complex expression before, during or after a treatment protocol, e.g., vaccination with peptides, antigen presenting cells, HLA/peptide tetramers, adoptive transfer or chemotherapy. The antibodies and antibody fragments of this invention may be coupled to diagnostic labeling agents for imaging of cells and tissues that express the HLA/peptide complexes or may be coupled to therapeutically useful agents by using standard methods well-known in the art. The antibodies also may be coupled to labeling agents for imaging e.g., radiolabels or fluorescent labels, or may be coupled to, e.g., biotin or anti-tumor agents, e.g., radioiodinated compounds, toxins such as ricin, methotrexate, cytostatic or cytolytic drugs, etc. Examples of diagnostic agents suitable for conjugating to the antibodies of this invention include e.g., barium sulfate, diatrizoate sodium, diatrizoate meglumine, iocetamic acid, iopanoic acid, ipodate calcium, metrizamide, tyropanoate sodium and radiodiagnostics including positron emitters such as fluorine-18 and carbon-11, gamma emitters such as iodine-123, technitium-99m, iodine-131 and indium-111, nuclides for nuclear magnetic resonance such as fluorine and gadolinium. As used herein, "therapeutically useful agents" include any therapeutic molecule which are preferably targeted selectively to a cell expressing the HLA/peptide complexes, including antineoplastic agents, radioiodinated compounds, toxins, other cytostatic or cytolytic drugs. Antineoplastic therapeutics are well known and include: aminoglutethimide, azathioprine, bleomycin sulfate, busulfan, carmustine, chlorambucil, cisplatin, cyclophosphamide, cyclosporine, cytarabidine, dacarbazine, dactinomycin, daunorubicin, doxorubicin, taxol, etoposide, fluorouracil, interferon-.alpha., lomustine, mercaptopurine, methotrexate, mitotane, procarbazine HCl, thioguanine, vinblastine sulfate and vincristine sulfate. Additional antineoplastic agents include those disclosed in Chapter 52, Antineoplastic Agents (Paul Calabresi and Bruce A. Chabner), and the introduction thereto, 1202-1263, of Goodman and Gilman's "The Pharmacological Basis of Therapeutics", Eighth Edition, 1990, McGraw-Hill, Inc. (Health Professions Division). Toxins can be proteins such as, for example, pokeweed anti-viral protein, cholera toxin, pertussis toxin, ricin, gelonin, abrin, diphtheria exotoxin, or *Pseudomonas* exotoxin. Toxin moieties can also be high energy-emitting radionuclides such as cobalt-60. The antibodies may be administered to a subject having a pathological condition characterized by the presentation of the HLA/peptide complexes of this invention, e.g., melanoma or other cancers, in an amount sufficient to alleviate the symptoms associated with the pathological condition.

Soluble T cell receptors (TcR) which specifically bind to the HLA/peptide complexes described herein are also an aspect of this invention. In their soluble form T cell receptors are analogous to a monoclonal antibody in that they bind to HLA/peptide complex in a peptide-specific manner. Immobilized TcRs or antibodies may be used to identify and purify unknown peptide/HLA complexes which may be involved in cellular abnormalities. Methods for identifying and isolating soluble TcRs are known in the art, see for example WO 99/60119, WO 99/60120 (both incorporated herein by reference) which describe synthetic multivalent T cell receptor complex for binding to peptide-MHC complexes. Recombinant, refolded soluble T cell receptors are specifically described. Such receptors may be used for delivering therapeutic agents or detecting specific peptide-MHC complexes expressed by tumor cells. WO 02/088740 (incorporated by reference) describes a method for identifying a substance that binds to a peptide-MHC complex. A peptide-MHC complex is formed between a predetermined MHC and peptide known to bind to such predetermined MHC. The complex is then use to screen or select an entity that binds to the peptide-MHC complex such as a T cell receptor. The method could also be applied to the selection of monoclonal antibodies that bind to the predetermined peptide-MHC complex.

Also a part of this invention are nucleic acid molecules encoding the antibodies and T cell receptors of this invention and host cells, e.g., human T cells, transformed with a nucleic acid molecule encoding a recombinant antibody or antibody fragment, e.g., scFv or Fab, or a TcR specific for a predesignated HLA/peptide complex as described herein, particularly a complex wherein the HLA molecule is an HLA-A2, A3, A26, HLA-B7, B8, B15, B27, B35, B44, B51 or B57 molecule, preferably HLA-A2 or B57, and the peptide has a nucleotide sequence set forth in SEQ ID NO: 1 (wherein X is Ala, Val, Leu, Ile, Pro, Phe, Met, Trp or Glu, preferably Val (SEQ ID NO: 3) or Ala (SEQ ID NO: 5)), 2, 3, 4, 5, 6, 7, 8, 9, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 77, 78, 88 (wherein X is absent (SEQ ID NO: 78) or any amino acid), 89, 106, 107 or 111. Preferably the peptide consists of the sequence set forth in SEQ ID NO: 1, SEQ ID NO: 2, SEQ ID NO: 3, SEQ ID NO: 5, SEQ ID NO: 77, SEQ ID NO: 78, SEQ ID NO: 88, SEQ ID NO: 89, SEQ ID NO: 106, SEQ ID NO: 107 or SEQ ID NO: 111.

Recombinant Fab or TcR specific for a predesignated HLA/peptide complex in T cells have been described in, e.g., Willemsen et al., "A phage display selected Fab fragment with MHC class I-restricted specificity for MAGE-A1 allows for retargeting of primary human T lymphocytes" *Gene Ther.* 2001 November; 8(21):1601-8. and Willemsen et al., "Grafting primary human T lymphocytes with cancer-specific chimeric single chain and two chain TCR". *Gene Ther.* 2000 August; 7(16):1369-77. (both incorporated herein by reference) and have applications in an autologous T cell transfer setting. The autologous T cells, transduced to express recombinant antibody or TcR, may be infused into a patient having an pathological condition associated with cells expressing the HLA/peptide complex. The transduced T cells are administered in an amount sufficient to inhibit the progression or alleviate at least some of the symptoms associated with the pathological condition.

This invention also relates to a method for promoting regression or inhibiting progression of a tumor in a subject in need thereof wherein the tumor expresses a complex of HLA and peptide. The method comprises administering an antibody, antibody fragment or soluble T cell receptor, which specifically binds to the HLA/peptide complex, or by administering cells transduced so that they express those antibodies or TcR in amounts that are sufficient to promote the regression or inhibit progression of the tumor expressing the HLA/peptide complex, e.g., a melanoma or other cancer. Preferably the HLA is an HLA-A2, HLA-B57 or HLA-B44 and the peptide is a MAGE-C2 derived peptide preferably a peptide consisting of the sequences set forth in SEQ ID NO: 1 (wherein X is Ala, Val, Leu, Ile, Pro, Phe, Met, Trp or Glu, preferably Val (SEQ ID NO: 3) or Ala (SEQ ID NO: 5)), 2, 3, 4, 5, 6, 7, 8, 9, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 77, 78, 88 (wherein X is absent (SEQ ID NO: 78) or any amino acid), 89, 106, 107 or 111, or their analogs, and preferably the peptide consists of the sequence set forth in SEQ ID NO: 1, SEQ ID NO: 2, SEQ ID NO: 3, SEQ ID NO: 5, SEQ ID NO: 77, SEQ ID NO: 78, SEQ ID NO: 88, SEQ ID NO: 89, SEQ ID NO: 106, SEQ ID NO: 107 or SEQ ID NO: 111.

The antibodies, antibody fragments and soluble T cell receptors may be conjugated with, or administered in conjunction with, an antineoplastic agent, e.g., radioiodinated compounds, toxins such as ricin, methotrexate, or a cytostatic or cytolytic agent as discussed supra. See e.g., Pastan et al., *Biochem. Biophys. Acta*, 133:C1-C6 (1997), Lode et al., *Immunol. Res.* 21:279-288 (2000) and Wihoff et al. *Curr. Opin. Mo. Ther.* 3:53-62 (2001) (all incorporated herein by reference) for a discussion of the construction of recombinant immunotoxins, antibody fusions with cytokine molecules and bispecific antibody therapy or immunogene therapy.

EXAMPLES

Example 1

An invaded lymph node of patient EB 81 was resected and allowed to establish tumor line EB81-MEL.2. This cell line was used to stimulate autologous T lymphocytes in a classical mixed-lymphocyte tumor-cell culture. After cloning by limiting dilution, cytotoxic T lymphocyte (CTL) clone 606 C/22.2 was obtained. This clone lysed specifically EB81-MEL.2 cells, but not autologous EBV-transformed B lymphocytes (EB8-EBV) nor K562. However, it was not directed against the peptides used for vaccination, as it did not recognize EB81-EBV pulsed with these peptides. Anti-HLA-A2 antibody blocked the activation of the CTL by the melanoma cells and thus the CTL was restricted by HLA-A2. A series of allogeneic HLA-A2 tumor lines were then tested, and several were recognized by CTL 606 C/22.2, including melanomas AVL3-MEL, LB373-MEL and myeloma U266. This indicated that the antigen recognized by this CTL was present in several different tumors.

To identify the gene encoding this antigen, a cDNA library was prepared with mRNA extracted from EB81-MEL.2 cells using standard techniques. The library was divided into pools of about 100 bacterial clones. Plasmid DNA extracted from each pool was used to transfect 293-EBNA cells together with plasmid DNA encoding HLA-A2. CTL 606 C/22.2 was added to the transfected cells and TNF production was measured. A positive pool was cloned and a new series of transfections was performed to identify the positive cDNA clone. The sequence of that clone proved identical to the sequence of MAGE-C2, a cancer/germ line gene expressed in about 40% of melanomas (Lucas et al, *Int. J. Cancer*, 87:55-60 (2000); Gure et al., "CT10: A New Cancer-Testis (CT) Antigen Homologous To CT7 And The Mage Family, Identified By Representational-Difference Analysis" Int. J. Cancer 85:726-732 (2000); and U.S. patent application Ser. No. 09/066,281 filed Apr. 24, 1998, now U.S. Pat. No. 6,475,783 all incorporated herein by reference). The only difference between this new cDNA (MAGE-C2M) and the previously described MAGE-C2 cDNA is the presence in MAGE-C2M of a short intronic sequence that is not spliced out. This additional exon (SEQ ID NO: 75, 5'-GTTTCCCAGCAG ACAAACTC-CCTAGGAAGACAGGAGACCTGTGAGGC-CCTAGAGCACCACCT TAAGAGAAGAAGAGCT-3') is located in the 5' untranslated region and therefore does not affect the coding sequence.

To identify the antigenic peptide, several minigenes were constructed by amplifying different fragments of the MAGE-C2 cDNA by PCR. PCR products were cloned into plasmid vector pcDNA3.1/His by TOPO T/A cloning (Invitrogen, following manufacturer's instructions). Cos-7 cells were transfected with the different minigenes, CTL 606 C/22.2 was added and the TNF production was measured.

The results indicated that the peptide-coding sequence was within the last 211 nucleotides of the open reading frame of the MAGE-C2 DNA. Several candidate peptides bearing the binding motif for HLA-A2 were then synthesized and non-apeptide ALKDVEERV (SEQ ID NO: 3) was found capable of stimulating TNF release by CTL 606/22.2. The recognition of this peptide by CTL 66/22.2 was then confirmed in a lysis assay of autologous EB81-EBV cells pulsed with peptide ALKDVEERV (SEQ ID NO: 3) or with shorter peptides ALKDVEER (SEQ ID NO: 4) and LKDVEERV (SEQ ID NO: 2). Peptide ALKDVEERV (SEQ ID NO: 3) was recognized with half-maximal lysis at 1 ng/ml peptide. Peptide LKDVEERV (SEQ ID NO: 2) was recognized about 30 times less efficiently.

SK23-MEL cells express HLA-A2 but do not express MAGE-C2. These cells were stably transfected with pcDNA3 containing a cDNA (SEQ ID NO: 72) encoding MAGE-C2 (SEQ ID NO: 71) by calcium-phosphate transfection. Transfected cells were selected with G418 (500 ug/ml), and cloned by limiting dilution. CTL 606 C/22.2 was stimulated by the transfected cells for 18 hours, then the concentration of TNF in the supernatant was measured by testing its toxicity for WEHI-164.13 cells. Clones of transformed SK23-MEL cells, SK23-MEL/MAGE-C2c13, SK23-MEL/MAGE-C2c12, SK23-MEL/MAGE-C2c11 were recognized by CTL 606C/22.2.

Example 2

Clinical Evolution of Patient EB81

EB 81 is a melanoma patient who showed complete regression of multiple cutaneous metastases after vaccination with a recombinant canary poxvirus (ALVAC) encoding MAGE-1.A1 and MAGE-3.A1 peptides and with synthetic MAGE-1.A1 (EADPTGHSY, SEQ ID NO: 10) and MAGE-3.A1 (EVDPIGHLY, SEQ ID NO: 11) peptides. The patient expressed both HLA-A1 and HLA-A2 alleles A*0101 and *0201 and HLA-B50, HLA-B57 and HLA-C6.

In April 1999 a primary cutaneous melanoma was surgically excised from the right ankle of patient EB81. Cutaneous metastases appeared in patient EB81 in June 1999. One of these cutaneous metastases was excised and found to contain melanoma cells expressing gene MAGE-3. Because the patient was initially typed as HLA-A1, she was vaccinated with a recombinant canarypox virus of the ALVAC type containing a minigene encoding the MAGE-1.A1 and MAGE-3.A1 peptides. Four injections of ALVAC, between September and November 1999, were followed by vaccinations with peptides MAGE-1.A1 and MAGE-3.A1, injected subcutaneously and intradermally without adjuvant. When vaccination was initiated, the patient had about 65 cutaneous metastases. About a third of these tumors started to regress during vaccination with ALVAC, while the others regressed later, during vaccination with the peptides. Two regressing metastases were resected, and all the others were undetectable by June and July 2000, ten months after the first vaccination. The patient did not receive any other anti-cancer treatment, except for a resection in April 2000 of an enlarged inguinal lymph node, which contained tumor cells expressing genes MAGE-1 and MAGE-3. Subsequently, the remaining lymph nodes of the same region were removed, but none of them contained melanoma cells. As of September 2002, the patient was still free of detectable melanoma.

Clonotypic PCR for the TCR of the Anti-MAGE-C2.A2 CTL Clone 606C/22.2.

The T cell receptor (TCR) of the anti-MAGE-C2.A2 CTL clone 606C/22.2 corresponds to Vα2-Jα6 and Vβ28-Jβ1-6 rearranged products. Clonotypic PCRs (Coulie et al., "A monoclonal cytolytic T-lymphocyte response observed in a melanoma patient vaccinated with a tumor-specific antigenic peptide encoded by gene MAGE-3" *PNAS* 28:10290-10295, 2001 incorporated herein by reference) were designed to assay for each of these two chains.

cDNA of RNA extracted with Tripure reagent (Gibco) from groups of peripheral blood mononuclear cells (PBMC), or from cells of a microdissected tumor, was prepared using an oligodT oligonucleotide containing a T7 promoter sequence. A fraction (1/100) of the cDNA was then used as template in three successive rounds of nested PCR using various primers to detect either the TCRα or the TCRβ rearranged product. PCR products were visualized on ethidium bromide-stained agarose gels using standard techniques.

The frequency of CTL 606C/22.2 to CD8 cells was determined in samples of PBMCs collected from patient EB81 in March 2000, 6 months after the first vaccination with recombinant ALVAC and peptides. cDNA of RNA extracted from 14 groups of 66,000 PBMCs, containing 17% CD8 T lymphocytes, was prepared and used as template in the TCRα and TCRβ clonotypic PCRs. Nine groups of the PBMCs were positive in both PCRs, indicating a frequency of anti-MAGE-C2.A2 CTL in the CD8 cells was about $9 \times 10^{-5}$. Four months later, the estimated frequency of anti-MAGE-C2.A2 CTL in the CD8 cells was $4 \times 10^{-5}$.

The presence of the anti-MAGE-C2.A2 CTL was also analyzed in the metastatic lymph node resected in April 2000, seven months after the first vaccination. Twenty circular sections (diameter±1 mm) were microdissected from this metastatic tumor and RNA extracted from cells of the microdissected sections was converted to cDNA. The cDNA used as template in a quantitative PCR for the CD8β gene product, and for the two clonotypic PCRs for CTL 606C/22.2. The results of the quantitative PCR for the CD8β gene product were used to estimate the number of CD8 T lymphocytes present in each microdissected section. All but two of the 20 microdissected sections contained CD8 cells, with estimated numbers varying from 1 to more than 600 cells (Table 3). The clonotypic PCR results indicated that CTL 606C/22.2 was present in all the microdissected sections that contained CD8 cells, even where the estimated number of CD8 cells in the section was lower than 10. These results indicate that in the tumor, the frequency of CTL 606C/22.2 in the CD8 cell population is about $10^{-1}$-$10^{-2}$. This frequency corresponded to an enrichment of at least 100-fold as compared to the frequency found in the PBMC sample. In contrast, when the frequency of anti-MAGE-3.A1 CTL in the CD8 cell population of the same lymph node was assayed by clonotypic PCR, the estimated CTL frequency proved similar to that found in the PBMC sample.

TABLE 3

Clonotypic PCR for CTL 606C/22.2 on fragments of tumor sections.

| Microdissected section | Number of CD8 cells in the section | Clonotypic PCR |
|---|---|---|
| 1 | 0 | − |
| 2 | 3 | + |
| 3 | 1 | + |
| 4 | 10 | + |
| 5 | 666 | + |
| 6 | 32 | + |
| 7 | 14 | + |
| 8 | 0 | + |
| 9 | 13 | + |
| 10 | 16 | + |
| 11 | 291 | + |
| 12 | 6 | + |
| 13 | 3 | + |
| 14 | 141 | + |
| 15 | 47 | + |
| 16 | 3 | + |
| 17 | 9 | + |
| 18 | 0 | − |
| 19 | 299 | + |
| 20 | 421 | + |

Example 3

Cytotoxic T lymphocyte (CTL) clone 606 C/21.7, was obtained by stimulating autologous CD8+ T lymphocytes with melanoma cell line EB81-MEL.2, which was derived from a lymph node metastasis resected from melanoma patient EB81 (HLA-A*0101, A*0201, B50, B57, C6). This patient was vaccinated with Mage-3.A1 nonapeptide EVD-PIGHLY, SEQ ID NO: 11 and recombinant canarypoxvirus (ALVAC) expressing this nonapeptide, and showed a complete regression of all metastatic lesions.

Autologous melanoma cell line EB81-MEL.2 is specifically lysed by CTL 606 C/21.7. Autologous EBV transformed B-cell line EB81-EBV, Mage 3-A1 peptide-pulsed EB81-EBV cells, and K562 cells were labeled with chromium and incubated with CTL at various effector-to-target ratios. $^{51}$Cr release was measured after 4 hours. Autologous melanoma cell line EB81-MEL.2, incubated with or without anti HLA-A,-B,-C, anti-HLA-B,-C or anti-HLA-A2, were used to stimulate CTL 606 C/21.7. After 18 hours of coculture, production of TNFα was measured by assaying the toxicity of the supernatants on WEHI-164.13 cells, which are TNFα-sensitive, using standard techniques (see Traversari et al., *Immunogenetics* 35: 145-152 (1992), incorporated herein by reference.). CTL 606 C/21.7 specifically lyses EB81-MEL.2 cells, and its HLA restriction is HLA-A2.

The CTL recognizes different allogeneic tumor cell lines expressing HLA-A2 e.g., melanoma lines AVL.3.MEL, and LB373-MEL and a myeloma cell line U266 indicating that the antigen recognized by CTL 606-C/21.7 is shared by those tumor cell lines. A non-small cell lung carcinoma cell line, LB37-NSCLC was not recognized by CTL 606 C/21.7.

To determine whether the HLA/peptide complex recognized by CTL 606 C/21.7 was encoded by a known gene, we transfected COS-7 cells with cDNAs corresponding to various genes known to be expressed in melanoma cells and that are known to produce antigenic peptides recognized by various CTLs. Transfected COS-7 cells were then assayed for their ability to induce TNFα production by CTL 606 C/21.7 to determine if they presented the HLA/peptide complex recognized by CTL 606 C/21.7. Cells transfected with cDNA encoding MAGE C2 were positive.

To localize the antigenic peptide, we produced truncated MAGE C2 cDNA fragments by PCR amplification using standard techniques, sub-cloned the cDNA fragments into the expression vector pcDNA3.1/Amp and transfected COS-7 cells with the expression vectors. A region of MAGE C2 encoding the antigenic peptide was comprised between positions 558 and 612 of the MAGE C2 cDNA, wherein position 1 is the ATG start codon at position 330 in SEQ ID NO: 72).

Several peptides were chosen in this region according to their affinity for HLA-A2 using the SYFPEITHI database at syfpeithi.bmi-heidelberg.com supra and the BIMAS database at bimas.dcrt.nih.gov/molbio/hlabind/index.html (Parker, K. C., et al., J. Immunol. 152:163., 1994). These peptides were tested for their ability to sensitize autologous EBV transformed B cells (EB81-EBV) such that they are lysed by CTL 606 C/21.7. Decamer peptide-LLFGLALIEV (SEQ ID NO: 77) was best recognized, with half-maximum lysis achieved at dose of 200 pg/ml. The negative control baseline level is 15%.

Three other independent CTL clones obtained by the same approach from the same patient were found to recognize the same peptide. The T cell receptor sequence of the 4 clones were different:

| CTL | T cell receptor |
| --- | --- |
| 606A/16.2 | Vβ9*01-Jβ2-7*01/02; |
| 606C/18.6 | Vβ2*01-Jβ2-7*01; |
| 606C/19.3 | Vβ7-9*01-Jβ2-1*01; |
| 606C/21.7 | Vβ15-2*01-Jβ2-3*01 |

TABLE 4

Homologs to the Mage-C2 peptide

| Protein | Peptide | Ligation strength* | SEQ ID NO: |
| --- | --- | --- | --- |
| Mage-C2 | LLFGLALIEV | 31 | 77 |
| Mage-C1 | ILFGISLREV | 31 | 82 |
| Mage-A10 | LVFGIDVKEV | 24 | 83 |
| Mage-C3 | LIFGIALTDM | 21 | 84 |
| Mage-B4 | LVFGLALKEV | 24 | 85 |
| Mage-A11 | LLFGIDVKEV | 30 | 86 |
| Mage-B4 | VVFGLELNKV | 25 | 87 |

*Ligation strength to HLA-A*0201 according to the SYFPEITHI database (syfpeithi.bmi-heidelberg.com) supra.
Peptide SEQ ID NOs from top to bottom of Table 4 are SEQ ID NO: 77, 83, 84, 85, 86 and 87.

Example 4

Cytotoxic T lymphocyte (CTL) clone 606 C/17.3, was obtained by stimulating peripheral blood CD8+ T lymphocytes with melanoma cell line EB81-MEL.2, which was derived from a lymph node metastasis resected from melanoma patient EB81 (HLA-A*0101, A*0201, B50, B57, C6) as disclosed in Examples 2 and 3.

CTL 606 C/17.3 specifically lyses EB81-MEL.2 cells as assayed by chromium release. Autologous EBV transformed B cell line EB81-EBV and K562 cells were used as control targets. Target cells were labeled with chromium and incubated with CTL at different effector-to-target ratios. $^{51}$Cr release was measured after 4 hours. Its HLA restriction was identified by analyzing the inhibitory effect of specific anti-HLA monoclonal antibodies (mAbs) on the recognition of EB81-MEL.2 cells. Autologous melanoma cell line EB81-MEL.2, alone or treated with specific antibodies against different HLA molecules, were used to stimulate CTL 606 C/17.3. After 18 hours of coculture, the production of TNF by CTL was measured by testing the toxicity of the supernatants on TNF-sensitive cell line WEHI-164.13. TNF production by CTL 606 C/17.3 was only blocked by anti-HLA-A.B.C and anti-HLA-B.C in this circumstance, but not by anti-HLA-A2 or anti-HLA-Bw6. This demonstrates that this CTL clone is HLA-B.C restricted and can be either HLA-B57 or HLA-C6, because HLA-B50 would be blocked by anti-HLA-Bw6 (anti-HLA-Bw6 blocks a range of different HLA-B types, among them HLA-B50, but not HLA-B57. See Marsh et al., The HLA Facts Book, Academic Press, 2000, incorporated herein by reference).

To determine the HLA restriction of CTL 606 C/17.3 and whether the antigen recognized by this CTL was encoded by a known gene, we transiently transfected COS-7 cells with plasmids containing cDNAs encoding various known proteins together with plasmids encoding either HLA-B57 or HLA-C6. Transfected cells were incubated with CTL for 18 hours and then the TNF in the supernatant was measured by its toxicity on TNF-sensitive cell line WEHI-164.13 as a measure of their ability to stimulate CTL 606 C/17.3. Among the cDNAs assayed, a MAGE C2-encoding DNA was positive when cotransfected with an HLA-B57-encoding cDNA. MAGE-C2 is expressed in about 40% of melanomas and also other types of tumors (S Lucas, Int. J. Cancer: 87, 55-60, 2002).

To assay recognition of different cell lines by CTL 606 C/17.3, HLA-B57 positive cell lines were used to stimulate CTL 606 C/17.3. After 18 hours of coculture, the production of TNF by CTL was measured by assaying the toxicity of the supernatants on the TNF-sensitive cell line WEHI-164.13. Tumor lines expressing MAGE-C2 and HLA-B57 were recognized by CTL 606 C/17.3.

To localize the antigenic peptide, we produced truncated MAGE-C2 cDNA fragments by PCR amplification, and cloned them into expression vector pcDNA3.1/Amp, "minigenes." We transiently transfected these minigenes into COS-7 cells together with the HLA-B57 cDNA. The transfected cells or EB81-MEL.2 cells were incubated with CTL for 18 hours and then TNF in the supernatants were measured by its toxicity on TNF-sensitive cell line WEHI-163.13. Using this we defined a region between nucleotide positions 120 and 309, counting from the start ATG of the open reading frame (ORF), of the MAGE-C2 cDNA (SEQ ID NO: 72) that encodes the antigenic peptide.

Several peptides within the region encoded by the nucleotide sequence between positions 120-309 of MAGE C2 (as above, counting begins at the first ATG of the ORF of the MAGE-C2 cDNA, SEQ ID NO: 72) were assayed for their ability to sensitize autologous EBV transformed B cells (EB81-EBV) to lysis by CTL 606 C/17.3. These peptides were selected with the aid of the SYFPEITHI database at syfpeithi.bmi-heidelberg.com supra. EB-81-EBV were labeled with $^{51}$Cr and then pulsed with peptides for 30 minutes at various concentrations. Thereafter, CTL 606 C/17.3 was added at an effector-to-target ratio of 10. Chromium release was measured after 4 hours of coincubation. Nonapeptide-ASSTLYLVF (SEQ ID NO: 89) was best recognized, with half-maximal lysis achieved at a dose around 10 ng/ml.

Example 5

LB2586 (BAGM) is a melanoma patient who received cycles of vaccination with autologous mature dendritic cells pulsed with peptide MAGE-3.A1. After 14 months of treatment, this patient displayed nearly complete regression of multiple cutaneous metastases. Regressions started after a first cycle of six injections. A second cycle of vaccinations was performed and additional metastases were seen to regress, while other metastases were stable. At 7 months after the starting of treatment, a cutaneous metastasis was surgically removed and part of the metastasis was used to establish tumor line BAGM-MEL.2.

Figure 1:
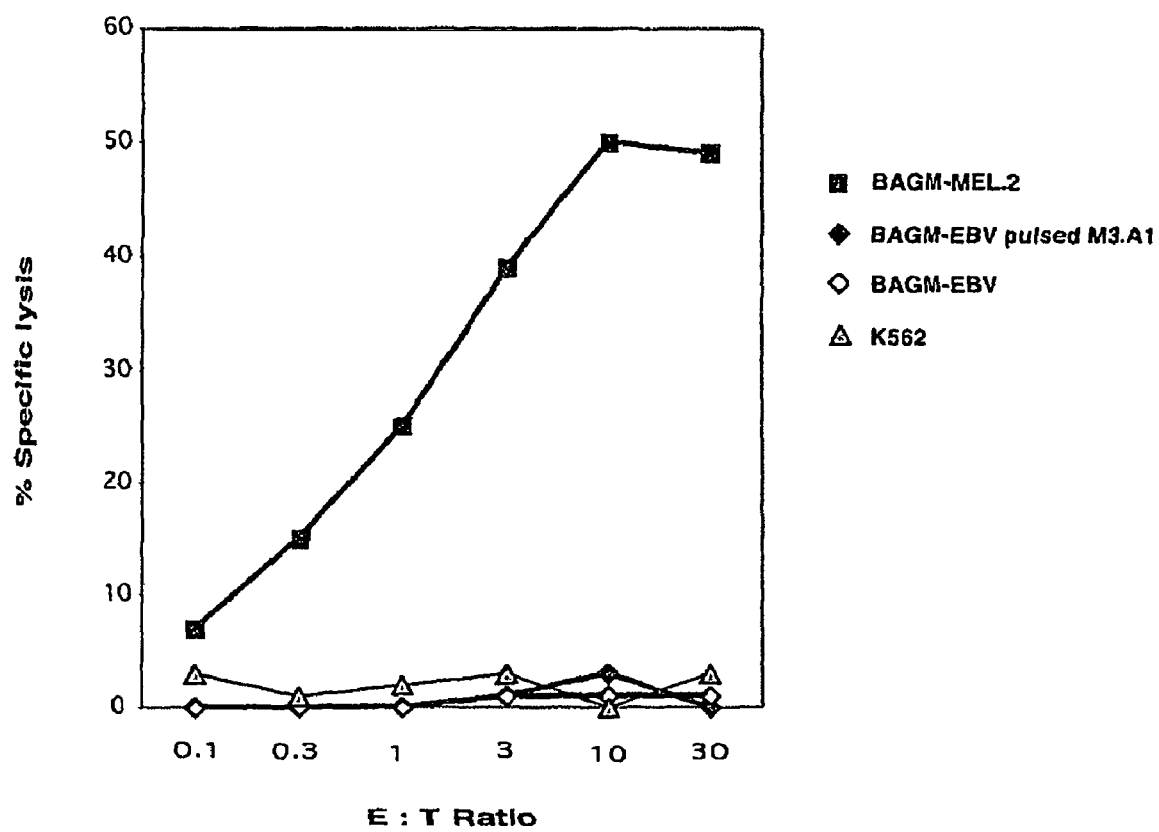
FIG. 1 depicts the specific lysis of target cells in a representative MLTC at day 14. Lymphocytes were incubated at various ratios with four target cells labeled with $Cr^{51}$. Non-labeled K562 cells were added at 50:1 to avoid non-specific lysis. The chromium release was measured after 4 hours. This figure shows one of the three MLTC and is representative of the others.

Pieces of the metastasis were cultured in macrowells containing culture medium comprising autologous serum and 100 U/ml of IL-2. After 14 days in culture, tumor infiltrating lymphocytes (TIL) were detected in nearly all the seeded wells. The TIL were pooled into three cultures and stimulated with the autologous tumor line in a classical mixed-lymphocyte-tumor-cell culture (MLTC). After 14 days, the three MLTC were tested in a $Cr^{51}$ release assay for lymphocytes having the ability to recognize specifically the autologous tumor cells, BAGM-MEL.2. Autologous BAGM-EBV transformed B cells and K562 cells were not recognized by the lymphocytes. Moreover, BAGM-EBV cells pulsed with peptide MAGE3.A1 were not lysed, suggesting that the lymphocytes which specifically recognized BAGM-MEL.2 cells were not directed against HLA complexes comprising the MAGE3.A1 peptide (FIG. 1).

Figure 2A:
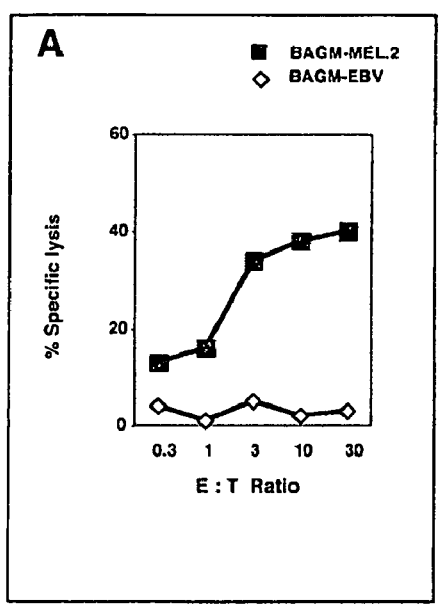
FIG. 2A depicts specific lysis of target cells by TIL clone 2.4. TIL cells were incubated at various ratios with $Cr^{51}$ labeled autologous BAGM-MEL.2 tumor cells that were treated with IFNγ (100 U/ml) for 48 hours and with $Cr^{51}$ labeled autologous EBV transformed B cells (BAGM-EBV). The chromium release was measured after 4 hours.
Figure 2B:
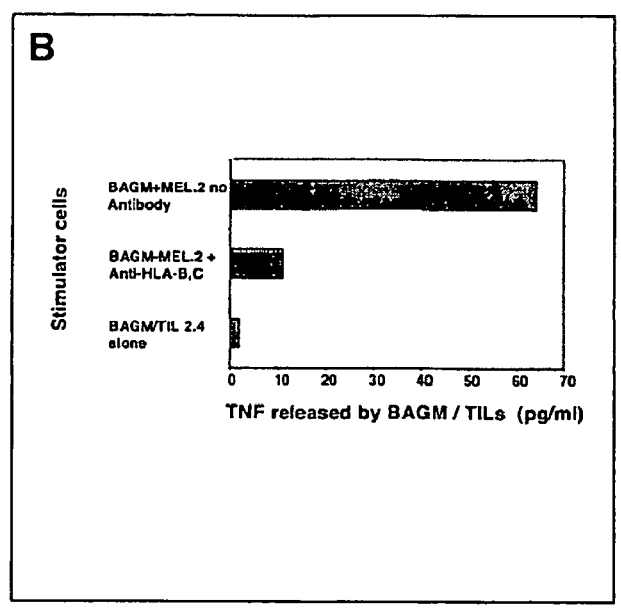
FIG. 2B depicts a TNF secretion assay. 1500 cells of the TIL clone were incubated with 20,000 autologous tumor cells pretreated with IFNγ as in FIG. 2A in microwells with medium containing IL-2 (12.5 U/ml final). In some wells, an antibody directed against HLA-B,-C molecules was added.

Clonotypic PCR to Identify the TCR of Clone TIL 2.4 and Identification of Antigenic Peptides Cytotoxic CD8+ TIL clones were obtained by limiting dilution cloning and their T cell receptors (TCR) were identified. One TIL clone having a Vβ19-Vα9 TCR was highly enriched in two MLTC assays. TIL 2.4 is an example clone expressing the Vβ19-Vα9 TCR. TIL 2.4 cells lysed the autologous tumor cells BAGM-MEL.2 (treated with IFNγ, 100 U/ml for 48 h) but did not lyse the autologous B-EBV cell line (FIG. 2A). TIL 2.4 also specifically secreted TNF upon incubation with the autologous tumor cells (FIG. 2B).

As a first step to characterize the antigenic peptide recognized by TIL 2.4, a TNF secretion assay was performed in the presence of anti-HLA antibodies. The results demonstrate that TNF production was inhibited by antibody B1.32.2, which recognized HLA-B molecules (HLA-B27 and B44), and HLA-C molecules (HLA-Cw2 and Cw16), of this patient (FIG. 2B).

The TIL were also incubated with COS-7 cells that were transiently transfected with plasmid containing cDNA of either HLA-B44, HLA-Cw2 or HLA-Cw16, together with one of a series of plasmids containing a cDNA for a known tumor antigen. Upon addition of TIL 2.4, secretion of TNF was obtained only with COS cells cotransfected with HLA-B44 and the MAGE-C2 cDNA, (the MAGE-C2 gene is expressed in about 40% of melanomas, S. Lucas, *Int. J. Cancer:* 87, 55-60, 2000).

To identify the antigenic peptide, several minigenes were generated by amplifying different fragments of the MAGE-C2 cDNA by PCR. The PCR products were cloned into plasmid vector pcDNA3.1/His by TOPO T/A cloning (MAGE-C2/HLA-A2 patent and Ma W et al., *Int. J. Cancer*: in press, incorporated herein by reference). COS-7 cells were transfected with vectors encoding HLA-B44 and vectors encoding the different minigenes described above. TIL 2.4 were added to the transfected cells and TNF production was measured (FIG. 3X). The results indicated that only minigenes 1 and 2, which comprise the 3' end of the open reading from of the MAGE-C2 gene, were recognized. These results indicated that the sequence encoding the peptide recognized by TIL2.4 was included in the 3'-end of the open reading frame of the MAGE-C2 gene. Candidate peptides bearing the binding motif for HLA-B44 were then synthesized and pulsed onto BAGM-EBV cells. These pulsed cells were combined with TIL2.4 and assayed for lysis. BAGM-EBV pulsed with an 11 amino acid peptide SESIKKKVLEF (SEQ ID NO: 106) containing two overlapping candidates, a nonapeptide SESIKKKVL (SEQ ID NO: 107: amino acids 307-315 MAGE C2) and a decapeptide ESIKKKVLEF (SEQ ID NO: 108: amino acids 308-317 of MAGE C2), were lysed by TIL 2.4 (FIG. 4X). The nonapeptide and the decapeptide were then synthesized and assayed individually. As shown in FIG. 4X, TIL 2.4 lysed BAGM-EBV cells pulsed with the nonapeptide SESIKKKVL, SEQ ID NO: 107: 50% maximum lysis was obtained at a concentration of 300 nM. No lysis was observed with the decapeptide ESIKKKVLEF (SEQ ID NO: 108). Similarly, the two octapeptides ESIKKKVL (SEQ ID NO: 109) and SESIKKKV (SEQ ID NO: 110), corresponding to the nonapeptide truncated at either end, failed to induce lysis.

In conclusion, the nonapeptide SESIKKKVL (SEQ ID NO: 107) is a MAGE.C2 antigenic peptide that binds to HLA-B*4403 and is recognized by BAGM-TIL of this invention (see FIG. 3X). This peptide is a previously unknown tumor antigen useful in diagnostic assays and immunotherapy of melanoma patients.

It has been reported that homologous antigenic peptides derived from different members of the MAGE family, e.g., the homologous peptides from Mage-A1 (EADPTGHSY SEQ ID NO: 10) and MAGE-A3 (EVDPIGHLY SEQ ID NO: 11) form complexes with HLA molecules that are recognized by T cells. (see U.S. Pat. No. 5,405,940). The MAGE-C2 peptide SESIKKKVL SEQ ID NO: 107, which is naturally processed and presented by HLA-B44 on the surface of tumor cells and recognized by specific T cells, has a homolog in MAGE-C1, i.e., SEVIKRKVV (SEQ ID 111). Gure et al. and Chen et al. infra report that some cancer patients display both a T cell response and a humoral response to MAGE-C2 (CT10) (SEQ ID NO: 71) and to MAGE-C1 (CT7) (SEQ ID NO: 73) demonstrating the strong immunogenic properties of these MAGE proteins (Gure et al., *Int. J. Canc.* 85:726-732 (2002) and Chen et al. *PNAS* 95(12):6919-6923 (1998)). Based on the disclosure herein, we expect that homologs of the MAGE-C2 peptide SESIKKKVL (SEQ ID NO: 107) that are found in other MAGE family members will also be antigenic, forming complexes with HLA molecules that will be recognized by cytolytic T cells. In particular, we expect that the MAGE-C1 peptide (SEQ ID NO: 111), will be presented by HLA-B44 and be recognized by T cells. As such this MAGE-C1 peptide and its use in diagnostic and therapeutic assays as disclosed herein are also a part of this invention.

We claim:

1. An isolated nucleic acid molecule consisting of a nucleotide sequence which encodes the peptide consisting of amino acid sequence SESIKKKVL (SEQ ID NO: 107).

2. An expression vector comprising an isolated nucleic acid molecule of claim 1.

3. A recombinant cell transformed or transfected with the isolated nucleic acid molecule of claim 1.

4. A recombinant cell transformed or transfected with the expression vector of claim 2.

* * * * *